US009650686B2

(12) United States Patent
Curvers et al.

(10) Patent No.: US 9,650,686 B2
(45) Date of Patent: May 16, 2017

(54) **EXTREME THERMOPHILIC BACTERIA OF THE GENUS *CALDICELLULOSIRUPTOR***

(71) Applicant: DIREVO INDUSTRIAL BIOTECHNOLOGY GMBH, Köln (DE)

(72) Inventors: Simon Curvers, Köln (DE); Vitaly Svetlichnyi, Köln (DE)

(73) Assignee: DIREVO Industrial Biotechnology GmbH, Cologne (DE)

( * ) Notice: Subject to any disclaimer, the term of this patent is extended or adjusted under 35 U.S.C. 154(b) by 0 days.

(21) Appl. No.: 14/880,743

(22) Filed: Oct. 12, 2015

(65) Prior Publication Data

US 2016/0024603 A1    Jan. 28, 2016

Related U.S. Application Data

(63) Continuation of application No. 14/342,712, filed as application No. PCT/EP2012/068627 on Sep. 21, 2012, now abandoned.

(60) Provisional application No. 61/669,981, filed on Jul. 10, 2012, provisional application No. 61/537,892, filed on Sep. 22, 2011.

(30) Foreign Application Priority Data

Sep. 22, 2011   (EP) .................................... 11007706
Jul. 10, 2012    (EP) .................................... 12175679

(51) Int. Cl.

| | | |
|---|---|---|
| *C12P 7/62* | (2006.01) | |
| *C12P 7/56* | (2006.01) | |
| *C12P 7/54* | (2006.01) | |
| *C12N 1/00* | (2006.01) | |
| *C12N 1/20* | (2006.01) | |
| *C12R 1/01* | (2006.01) | |
| *C12P 3/00* | (2006.01) | |
| *C12P 7/06* | (2006.01) | |
| *C12P 7/10* | (2006.01) | |
| *C12P 7/40* | (2006.01) | |

(52) U.S. Cl.
CPC ................ *C12R 1/01* (2013.01); *C12N 1/20* (2013.01); *C12P 3/00* (2013.01); *C12P 7/065* (2013.01); *C12P 7/10* (2013.01); *C12P 7/40* (2013.01); *C12P 7/54* (2013.01); *C12P 7/56* (2013.01); *C12P 7/62* (2013.01); *C12P 2201/00* (2013.01); *Y02E 50/16* (2013.01); *Y02E 50/17* (2013.01)

(58) Field of Classification Search
CPC .... C12N 1/20; C12P 3/00; C12P 7/065; C12P 7/54; C12P 7/56; C12P 7/10; C12P 7/40; C12P 2201/00; C12P 7/62; Y02E 50/16; Y02E 50/17; C12R 1/01

USPC .............. 435/135, 139, 140, 243, 253.6
See application file for complete search history.

(56) References Cited

U.S. PATENT DOCUMENTS

| | | | |
|---|---|---|---|
| 8,278,087 B2 | 10/2012 | Remmereit et al. | |
| 8,435,770 B2 | 5/2013 | Hogsett et al. | |
| 2015/0140602 A1* | 5/2015 | Curvers | C12P 39/00 435/42 |

FOREIGN PATENT DOCUMENTS

WO   WO 2010/075213 A2 *   7/2010   .............. C12P 7/10

OTHER PUBLICATIONS

Kumar et al., Methods for pretreatment of lignocellulosic biomass for efficeint hydrolysis and biofuel production. Ind. Eng. Chem., 2009, vol. XXXX, xxx, 000: pp. A-Q.*
Rainey F A et al: "Phylogenetic Analysis of Anaerobic Thermophilic Bacteria: Aid for their Reclassification," Journal of Bacteriology, American Society for Microbiology, Washington, DC; US, vol. 175, No. 15, Aug. 1, 1993, pp. 4772-4779.
Rainey F A et al: "Description of *Caldicellulosiruptor saccharolyticus* gen. nov., sp. nov: An obligately anaerobic, extremely thermophilic, cellulolytic bacterium," FEMS Microbiology Letters (no longer published by Elsevier), vol. 120, No. 3, Jul. 15, 1994, pp. 263-266.
Panagiotopoulos I A et al: "Fermentative hydrogen production from pretreated biomass: A comparative study," Bioresource Technology, Elsevier BV, GB, vol. 100, No. 24, Dec. 1, 2009, pp. 6331-6338.
Yang Sung-Jae et al: "Efficient Degradation of Lignocellulosic PLant Biomass, without Pretreatment, by the Thermophilic Anaerobe Anaerocellum thermophilum DSM 6725," Applied & Environmental Microbiology, American Society for Microbiology, US, vol. 75, No. 14, Jul. 1, 2009, pp. 4762-4769.
S.D. Hamilton-Brehm et al: "*Caldicellulosiruptor obsidiansis* sp. nov., an Anaerobic, Extremely Thermophilic, Cellulolytic Bacterium Isolated from Obsidian Pool, Yellowstone National Park," Applied & Environmental Microbiology, vol. 76, No. 4, Feb. 15, 2010, pp. 1014-1020.

(Continued)

*Primary Examiner* — Ganapathirama Raghu
(74) *Attorney, Agent, or Firm* — Wagenknecht IP Law Group PC

(57) ABSTRACT

A method for converting lignocellulosic biomass material to a carboxylic acid comprising the step of contacting the lignocellulosic biomass material with a microbial culture for a period of time at an initial temperature and an initial pH, thereby producing an amount of a carboxylic acid; wherein the microbial culture comprises an extremely thermophilic bacteria strain selected from the group consisting of *Caldicellulosiruptor* sp. DIB041C, *Caldicellulosiruptor* sp. DIB087C, *Caldicellulosiruptor* sp. DIB103C, *Caldicellulosiruptor* sp. DIB104C, *Caldicellulosiruptor* sp. DIB107C, *Caldicellulosiruptor* sp. DIB101C, and *Caldicellulosiruptor* sp. DIB004C, and wherein the lignocellulosic biomass material is converted in a single step process as part of a consolidated bioprocessing (CBP) system.

13 Claims, 11 Drawing Sheets

(56) References Cited

OTHER PUBLICATIONS

PCT/EP2012/068527 International Search Report mailed Mar. 28, 2013.
van de Werken et al. "Hydrogenomics of the Extremely Thermophilic Bacterium 'Caldicellulosiruptor saccharolyticus'." Applied and Environmental Microbiology, Nov. 2008, 74(21):6720-6729.

* cited by examiner

FIGURE 2

**16SrDNA consensus sequence for *Caldicellulosiruptor spec.* DIB004C (SEQ ID NO. 1)**

```
TTACGACTTC ACCCCAATCA TCAGCCCCAC CTTCAACACA GCTTAACCTG TGTCTTCAGG      60
TGTTGCTGAC TCTCATGGTG TGACGGGCGG TGTGTACAAG GCCCGGGAAC GTATTCACCG     120
CGGCATGCTG ATCCGCGATT ACTAGCGATT CCGACTTCAT GCAGGCGAGT TGCAGCCTGC     180
AATCCGAACT GGGGGTGCTT TTTTGGGATT CGCTCCGGCT CGCGCCTTCG CACGCCCTCT     240
GTAGCACCCA TTGTAGCACG TGTGTAGCCC AGGGCATAAG GGGCATGATG ATTTGACGTC     300
ATCCCCACCT TCCTCCGCCT CATCCACCGC AGTCCCCTTA GAGTGCCCAC CATTACCCCC     360
TGGCAACTAA GGGCAGGGGT TGCGCTCGTT GCGGGACTTA ACCCAACATC TCACGACACG     420
AGCTGACGAC AACCATGCAC CACCTGTGTC CGGGCTCCTG CTCTCATCGA ACAGGCACCC     480
CACCCTTTCC GGCAGGTCCC CGGCATCTCA AGCCCTGGTA ACGTTCTTCC CCTTGCTTCC     560
AATTAAACCA CATGCTCCAC CGCTTGTGCG GGCCCCCGTC AATTCCTTTG AGTTTCAACC     600
TTGCGGCCGT ACTCCCCAGG CGGGATGCTT ATTGTGTTAA CTACGGCACG GAGGAGTCCT     660
TCTCCCCCAC ACCTAGCATC CATCGTTTAC AGCGTGGACT ACCAGGGTAT CTAATCCTGT     720
TCGCTCCCCA CGCTTTCGTG CCTCAGCGTC AGTTACGGTC CAGACGGCCG CCTTCGCCAC     780
TGGTGTTCCT CCCGATATCT ACGCATTTCA CCGCTACACC GGGAATTCCG CCGTCCTCTC     840
CCGCACTCAA GCTATGCAGT ATTAAGCGCA ATCCTTAGGT TGAGCCTAAG GCTTTCACGC     900
TTAACTCGCA TAGCCGCCTA CGCACCCTTT ACGCCCAGTA ATTCCGGACA ACGCTCGGCA     960
CCTACGTATT ACCGCGGCTG CTGGCACGTA GTTAGCCGTG GCTTTTTAAA CGGGTACTAT    1020
CTCCTACTTC TCCCCGTCCA AAGAGGTTTA CACCCCGAAG GGCTTCTTCC CTCACGCGGC    1080
GTCGCTGCGT CAGGCTTCCG CCCATTGCGC AAGATTCCCC GCTGCTGCCT CCCGTAGGAG    1140
TGTGGGCCGT GTCTCAGTCC CACTGTGCC GTACACCCTC TCAGGCCGGC TACCCGTCGT    1200
CGCCTTGGTA GGCCGTTACC CCACCAACTA GCTGATGGGC CGCGAGCCCA TCCCCAGCCA    1260
GTATAGCCTC CCCGGCTACC CTTTCACCAC ATCACCATGC GATGACGTGG TCCCATCGGG    1320
TATTAGCAGC CCTTTCGAGC TGTTATCCCC GTGCTGGGGG TAGGTTGCTC ACGTGTTACT    1380
CACCCGTCCG CCGCTA                                                   1396
```

FIGURE 3

**16SrDNA consensus sequence for *Caldicellulosiruptor* sp. DIB041C (SEQ ID NO. 2)**

```
CTCAGGACGA ACGCTGGCGG CGTGCCTAAC GCATGCAAGT CGAGCGGAGG TAGCCATGAA      60
GGTGAACAGC TGGAGTGGCT ATCTTAGCGG CCGACGGGTG ACTAACACGT GAGCAACCTA     120
CCCTCAGCAC GGGGATAACA GCTCGAAAGG GCTGCTAATA CCCGATGGGA CCACGGCATC     180
GCATGATGTT GTGGTGAAAG GGTAGCCGTG GAGGCTATAC CGGCTGGGGA TGGGCTCGCG     240
GCCCATCAGC TAGTTGGTGG GGTAACGGCC TACCAAGGCT ACGACGGGTA GCCGGCCTGA     300
GAGGGTGGTC GGCCACAGTG GGACTGAGAC ACGGCCCACA CTCCTACGGG AGGCAGCAGC     360
GGGGAATCTT GCGCAATGGG CGAAAGCCTG ACGCAGCGAC GCCGCGTGAG GGAGGAAGCC     420
CTTCGGGGTG TAAACCTCTT TGGACGGGGA GAAGGAGGAG ATAGTACCCG TTTAAAAAGC     480
CACGGCTAAC TACGTGCCAG CAGCCGCGGT AATACGTAGG TGGCGAGCGT TGTCCGGAAT     540
TACTGGGCGT AAAGGGTGCG TAGGCGGCTA TGCAAGTTAA GCGTGAAATC TTGGGGCTCA     600
ACCCCAAGGC TGCGCTTAAT ACTGCATAGC TTGAGTGCGG GAGAGGACGG CGGAATTCCC     660
GGTGTAGCGG TGAAATGCGT AGATATCGGG AGGAACACCA GTGGCGAAGG CGGCCGTCTG     720
GACCGTAACT GACGCTGAGG CACGAAAGCG TGGGGAGCGA ACAGGATTAG ATACCCTGGT     780
AGTCCACGCT GTAAACGATG GATGCTAGGT GTGGGGAGA AGGACTCCTC CGTGCCGTAG     840
TTAACACAAT AAGCATCCCG CCTGGGGAGT ACGGCCGCAA GGTTGAAACT CAAAGGAATT     900
GACGGGCGCC CGCACAAGCC GTGGAGCATG TCGTTTAATT CCAAGCAACG CGAAGAACCT     960
TACCAGGGCT TGACATGCCG GGAACCTGCC CGAAAGGGTG GGGTGCCTGC GCGATGAGTG    1020
CAGGAGCCCG GACACAGGTG GTGCATGGTT GTCGTCAGCT CGTGTCGTGA GATGTTGGGT    1080
TAAGTCCCGC AACGAGCGCA ACCCTCGCCC TTAGTTGCCA GCACGTAATG GTGGGCACTC    1140
TAAGGGGACT GCCGCCGATG AGGCGAGGA AGGTGGGGAT GACGTCAAAT CATCATGCCC    1200
CTTATGCCCT GGGCTACACA CGTGCTACAA TGGGTGCTAC AGAGGGTTGC GAAGGCGCGA    1260
GCCGGAGCTA ATCCCAAAAA AGCACCCCA GTTCGGATTG CAGGCTGCAA CTCGCCTGCA    1320
TGAAGTCGGA ATCGCTAGTA ATCGCGGATC AGCATGCCGC GGTGAATACG TTCCCGGGCC    1380
TTGTACACAC CGCCCGTCAC ACCATGAGAG TCAGCAACAC CTGAAGCACG AGGGCAGCTG    1440
TGTTGAAGGT GGGGCTGATG ATTGGGGTGA AGTCGTAACA                           1580
```

FIGURE 4

**16SrDNA consensus sequence for *Caldicellulosiruptor* sp. DIB087C (SEQ ID NO. 3)**

```
TCAGGACGAA CGCTGGCGGC GTGCCTAACG CATGCAAGTC GAGCGGAGAT GGTGGTTGAA    60
GGTGATGAGC TGGAGGCTGC CATCTTAGCG GCGGACGGGT GAGTAACACG TGAGCAACCT   120
ACCCCCAGCA CGGGGATAAC AGCTCGAAAG GGCTGCTAAT ACCCGATGGG ACCACGTCAT   180
CGCATGGTGA TGTGGTGAAA GGGTAGCCGG GGAGGCTATA CTGGCTGGGG ATGGGCTCGC   240
GGCCCATCAG CTAGTTGGTG GGGTAACGGC TCACCAAGGC GACGACGGGT AGCCGGCCTG   300
AGAGGGTGTA CGGCCACAGT GGGACTGAGA CACGGCCCAC ACTCCTACGG GAGGCAGCAG   360
CGGGGAATCT TGCGCAATGG GCGGAAGCCT GACGCAGCGA CGCCGCGTGA GGGAAGAAGC   420
CCTTCGGGGT GTAAACCTCT TTGGACGGGG AGAAGTAGGA GATAGTACCC GTTTAAAAAG   480
CCACGGCTAA CTACGTGCCA GCAGCCGCGG TAATACGTAG GTGGCGAGCG TTGTCCGGAA   540
TTACTGGGCG TAAAGGGTGC GTAGGCGGCT ATGCGAGTTA AGCGTGAAAG CCTTAGGCTC   600
AACCTAAGGA TTGCGCTTAA TACTGCATAG CTTGAGTGCG GGAGAGGACG GCGGAATTCC   660
CGGTGTAGCG GTGAAATGCG TAGATATCGG GAGGAACACC AGTGGCGAAG GCGGCCGTCT   720
GGACCCTAAC TGACCCTGAG GCACCAAACC CTCCCGACCG AACACCATTA GATACCCTGG   780
TAGTCCACGC TGTAAACGAT GGATGCTAGG TGTGGGGAG AAGGACTCTT CCGTGCCGTA   840
GTTAACACAA TAAGCATCCC GCCTGGGGAG TACGGCCGCA AGGTTGAAAC TCAAAGGAAT   900
TGACGGGGGC CCGCACAAGC GGTGGAGCAT GTGGTTTAAT TCGAAGCAAC GCGAAGAACC   960
TTACCAGGGC TTGACATGCC GGGGACCTGC CCGAAAGGGT GGGGTGCCTG TTCGATGAGA  1020
CCACGAACCC CGACACACGT GGTGCATGGT TGTCGTCAGC TCGTGTCGTG AGATGTTGGG  1080
TTAAGTCCCG CAACGAGCGC AACCCCTGCC CTTAGTTGCC AGCGGGTAAT GGTGGGCACT  1140
CTAAGGGGAC TGCCGTCGAT GAGGCGGAGG AAGGTGGGGA TGACGTCAAA TCATCATGCC  1200
CCTTATGCCC TGGGCTACAC ACGTGCTACA ATGGGTGCTA CAGAGGGCGT GCGAAGGCGC  1260
GAGCCGGAGC GAATCCCAAA AAAGCACCCC CAGTTCGGAT TGCAGGCTGC AACTCGCCTG  1320
CATGAAGTCG GAATCGCTAG TAATCGCGGA TCAGCATGCC GCGGTGAATA CGTTCCCGGG  1380
CCTTGTACAC ACCGCCCGTC ACACCATGAG AGTCAGCAAC ACCTGAAGAC ACAGGTAAG   1440
CTGTGTTGAA GGTGGGGCTG ATGATTGGGG TGAAGTCGTA A                     1481
```

FIGURE 5

**16SrDNA consensus sequence for *Caldicellulosiruptor spec.* DIB101C (SEQ ID NO. 4)**

```
CCTGTGTCTT CAGGTGTTGC TGACTCTCAT GGTGTGACGG GCGGTGTGTA CAAGGCCCGG    60
CAACGTATTC ACCGCGGCAT GCTGATCCGC GATTACTAGC GATTCCGACT TCATGCAGGC   120
GAGTTGCAGC CTGCAATCCG AACTGGGGGT GCTTTTTTGG GATTCGCTCC GGCTCGCGCC   180
TTCGCACGCC CTCTGTAGCA CCCATTGTAG CACGTGTGTA GCCCAGGGCA TAAGGGGCAT   240
GATGATTTGA CGTCATCCCC ACCTTCCTCC GCCTCATCGA CGGCAGTCCC CTTAGAGTGC   300
CCACCATTAC GCGCTGGCAA CTAAGGGCAG GGGTTGCGCT CGTTGCGGGA CTTAACCCAA   360
CATCTCACGA CACGAGCTGA CGACAACCAT GCACCACCTG TGTCCGGGCT CCTGCTCTCA   420
TCGAACAGCC ACCCCACCCT TTCGCCCAGG TCCCCGGCAT GTCAAGCCCT GGTAAGGTTC   480
TTCGCGTTGC TTCGAATTAA ACCACATGCT CCACCGCTTG TGCGGGCCCC CGTCAATTCC   540
TTTGAGTTTC AACCTTGCGG CCGTACTCCC CAGGCGGGAT GCTTATTGTG TTAACTACGG   600
CACGGAGGAG TCCTTCTCCC CCACACCTAG CATCCATCGT TTACAGCGTG GACTACCAGG   660
GTATCTAATC CTGTTCGCTC CCCACGCTTT CGTGCCTCAG CGTCAGTTAC GGTCCAGACG   720
GCCGGCTTCG CCACTGGTGT TCCTCCCGAT ATCTACGCAT TTCACCGCTA CACCGGGAAT   780
TCCGCCGTCC TCTCCCGCAC TCAACCTATG CAGTATTAAG CCCAATCCTT AGCTTGACCC   840
TAAGGCTTTC ACGCTTAACT CGCATAGCCG CCTACGCACC CTTTACGCCC AGTAATTCCG   900
GACAACGCTC GCCACCTACG TATTACCGCG GCTGCTGGCA CGTAGTTAGC CGTGGCTTTT   960
TAAACGGGTA CTATCTCCTA CTTCTCCCCG TCCAAAGAGG TTTACACCCC GAAGGGCTTC  1020
TTCCCTCACG CGGCGTCGCT GCGTCAGGCT TCCGCCCATT GCGCAAGATT CCCCGCTGCT  1080
CCCTCCCTA GCAGTGTGGG CCCTCTCTCA GTCCCACTGT GGCCGTACAC CCTCTCAGCC  1140
CGGCTACCCG TCGTCGCCTT GGTAGGCCGT TACCCCACCA ACTAGCTGAT GGGCCGCGAG  1200
CCCATCCCCA GC                                                     1212
```

FIGURE 6

**16SrDNA consensus sequence for *Caldicellulosiruptor* sp. DIB103C (SEQ ID NO. 5)**

```
CGACTTCACC CCAATCATCA GCCCCACCTT CAACACAGCT TAACCTGTGT CTTCAGGTGT    60
TGCTGACTCT CATGGTGTGA CGGGCGGTGT GTACAAGGCC CGGGAACGTA TTCACCGCGG   120
CATGCTGATC CGCGATTACT AGCGATTCCG ACTTCATGCA GGCGAGTTGC AGCCTGCAAT   180
CCGAACTGGG GGTGCTTTTT TGGGATTCGC TCCGCTCGC GCCTTCGCAC GCCCTCTGTA    240
GCACCCATTG TAGCACGTGT GTAGCCCAGG GCATAAGGGG CATGATGATT TGACGTCATC   300
CCCACCTTCC TCCGCCTCAT CGACGGCAGT CCCCTTAGAG TGCCCACCAT TACGCGCTGG   360
CAACTAAGGG CAGGGGTTGC GCTCGTTGCG GGACTTAACC CAACATCTCA CGACACGAGC   420
TGACGACAAC CATGCACCAC CTGTGTCCGG GCTCCTGCTC TCATCGAACA GGCACCCCAC   480
CCTTTCGGGC AGGTCCCCGG CATGTCAAGC CCTGGTAAGG TTCTTCGCGT TGCTTCGAAT   540
TAAACCACAT GCTCCACCGC TTGTGCGGGC CCCCGTCAAT TCCTTTGAGT TTCAACCTTG   600
CGGCCGTACT CCCCAGGCGG GATGCTTATT GTGTTAACTA CGGCACGGAG GAGTCCTTCT   660
CCCCCACACC TAGCATCCAT CGTTTACAGC GTGGACTACC AGGGTATCTA ATCCTGTTCG   720
CTCCCCACGC TTTCGTGCCT CAGCGTCAGT TACGGTCCAG ACGGCCGCCT TCGCCACTGG   780
TGTTCCTCCC GATATCTACG CATTTCACCG CTACACCGGG AATTCCGCCG TCCTCTCCCG   840
CACTCAAGCT ATGCAGTATT AAGCGCAATC CTTAGGTTGA GCCTAAGGCT TTCACGCTTA   900
ACTCGCATAG CGCCTACGC ACCCTTTACG CCCAGTAATT CCGGACAACG CTCGCCACCT    960
ACGTATTACC GCGGCTGCTG GCACGTAGTT AGCCGTGGCT TTTTAAACGG GTACTATCTC  1020
CTACTTCTCC CCGTCCAAAG AGGTTTACAC CCCGAAGGGC TTCTTCCCTC ACGCGGCGTC  1080
GCTGCGTCAG GCTTCCGCCC ATTGCGCAAG ATTCCCCGCT GCTGCCTCCC GTAGGAGTGT  1140
GGGCCGTGTC TCAGTCCCAC TGTGGCCGTA CACCCTCTCA GGCCGGCTAC CCGTCGTCGC  1200
CTTGGTAAGC CGTTACCCCA CCAACTAGCT GATGGGCCGC GAGCCCATCC CCA         1253
```

FIGURE 7

**16SrDNA consensus sequence for *Caldicellulosiruptor* sp. DIB104C (SEQ ID NO. 6)**

```
GACTTCACCC CAATCATCAG CCCCACCTTC AACACAGCTT AACCTGTGTC TTCAGGTGTT    60
GCTGACTCTC ATGGTGTGAC GGGCGGTGTG TACAAGGCCC GGGAACGTAT TCACCGCGGC   120
ATGCTGATCC GCGATTACTA GCGATTCCGA CTTCATGCAG GCGAGTTGCA GCCTGCAATC   180
CGAACTGGGG GTGCTTTTTT GGGATTCGCT CCGGCTCGCG CCTTCGCACG CCCTCTGTAG   240
CACCCATTGT AGCACGTGTG TAGCCCAGGG CATAAGGGGC ATGATGATTT GACGTCATCC   300
CCACCTTCCT CCGCCTCATC GACGGCAGTC CCCTTAGAGT GCCCACCATT ACGCGCTGGC   360
AACTAAGGGC AGGGGTTGCG CTCGTTGCGG GACTTAACCC AACATCTCAC GACACGAGCT   420
GACGACAACC ATGCACCACC TGTGTCCGGG CTCCTGCTCT CATCGAACAG GCACCCCACC   480
CTTTCGGGCA GGTCCCCGGC ATGTCAAGCC CTGGTAAGGT TCTTCGCGTT GCTTCGAATT   540
AAACCACATG CTCCACCGCT TGTGCGGGCC CCCGTCAATT CCTTTGAGTT TCAACCTTGC   600
GGCCGTACTC CCCAGGCGGG ATGCTTATTG TGTTAACTAC GGCACGGAAG AGTCCTTCTC   660
CCCCACACCT AGCATCCATC GTTTACAGCG TGGACTACCA GGGTATCTAA TCCTGTTCGC   720
TCCCCACGCT TTCGTGCCTC AGCGTCAGTT ACGGTCCAGA CGGCCGCCTT CGCCACTGGT   780
GTTCCTCCCG ATATCTACGC ATTTCACCGC TACACCGGGA ATTCCGCCGT CCTCTCCCGC   840
ACTCAAGCTA TGCAGTATTA AGCGCAATCC TTAGGTTGAG CCTAAGGCTT TCACGCTTAA   900
CTCCCATACC CGCCTACCCA CCCTTTACCC CCACTAATTC CCCACAACGC TCGCCACCTA   960
CGTATTACCG CGGCTGCTGG CACGTAGTTA GCCGTGGCTT TTTAAACGGG TACTATCTCC  1020
TACTTCTCCC CGTCCAAAGA GGTTTACACC CCGAAGGGCT TCTTCCCTCA CGCGGCGTCG  1080
CTGCGTCAGG CTTCCGCCCA TTGCGCAAGA TTCCCCGCTG CTGCCTCCCG TAGGAGTGTG  1140
GGCCGTGTCT CAGTCCCACT GTGGCCGTAC ACCCTCTCAG GCCGGCTACC CGTCGTCGCC  1200
TTGGTGAGCC GTTACCCCAC CAACTAGCTG ATGGGCCGCG AGCCCATCCC CAGCC       1255
```

Figure 8

**16SrDNA consensus sequence for *Caldicellulosiruptor* sp. DIB107C (SEQ ID NO. 7)**

```
GACTTCACCC CCAATCATCA GCCCCACCTT CAACACAGCT TAACCTGTGT CTTCAGGTGT      60
TGCTGACTCT CATGGTGTGA CGGGCGGTGT GTACAAGGCC CGGGAACGTA TTCACCGCGG     120
CATGCTGATC CGCGATTACT AGCGATTCCG ACTTCATGCA GGCGAGTTGC AGCCTGCAAT     180
CCGAACTGGG GGTGCTTTTT TGGGATTCGC TCCGGCTCGC GCCTTCGCAC GCCCTCTGTA     240
GCACCCATTG TAGCACGTGT GTAGCCCAGG GCATAAGGGG CATGATGATT TGACGTCATC     300
CCCACCTTCC TCCGCCTCAT CGACGGCAGT CCCCTTAGAG TGCCCACCAT TACGCGCTGG     360
CAACTAAGGG CAGGGGTTGC GCTCGTTGCG GGACTTAACC CAACATCTCA CGACACGAGC     420
TGACGACAAC CATGCACCAC CTGTGTCCGG GCTCCTGCTC TCATCGAACA GGCACCCCAC     480
CCTTTCGGGC AGGTCCCCGG CATGTCAAGC CCTGGTAAGG TTCTTCGCGT TGCTTCGAAT     540
TAAACCACAT GCTCCACCGC TTGTGCGGGC CCCCGTCAAT TCCTTTGAGT TTCAACCTTG     600
CGGCCGTACT CCCCAGGCGG GATGCTTATT GTGTTAACTA CGGCACGGAG GAGTCCTTCT     660
CCCCCACACC TAGCATCCAT CGTTTACACC GTGGACTACC AGGGTATCTA ATCCTCTTCG     720
CTCCCCACGC TTTCGTGCCT CAGCGTCAGT TACGGTCCAG ACGGCCGCCT TCGCCACTGG     780
TGTTCCTCCC GATATCTACG CATTTCACCG CTACACCGGG AATTCCGCCG TCCTCTCCCG     840
CACTCAAGCT ATGCAGTATT AAGCGCAATC CTTAGGTTGA GCCTAAGGCT TTCACGCTTA     900
ACTCGCATAG CCGCCTACGC ACCCTTTACG CCCAGTAATT CCGGACAACG CTCGCCACCT     960
ACGTATTACC GCGGCTGCTG GCACGTAGTT AGCCGTGGCT TTTTAAACGG GTACTATCTC    1020
CTACTTCTCC CCGTCCAAAG AGGTTTACAC CCCGAAGGGC TTCTTCCCTC ACGCGGCGTC    1080
GCTGCGTCAG GCTTCCGCCC ATTGCGCAAG ATTCCCCGCT GCTGCCTCCC GTAGGAGTGT    1140
GGGCCGTGTC TCAGTCCCAC TGTGGCCGTA CACCCTCTCA GGCCGGCTAC CCGTCGTCGC    1200
CTTGGTGAGC CGTTACCTCA CCAACTAGCT GATGGGCCGC GAGCCCATCC CCAGCCGGAT    1260
TACTCCTTTC ACCACATCAC CATGCGATGA CGTGGTCCCA TCGGGTATTA GCAGCCCTTT    1320
CGAGCTGTTA TCCCCGTGCT GGGGGTAGGT TGCTCACGTG TTACTCACCC GTCCGCCGCT    1380
AAGATGGCAG CCTCCAGCTC ATCACCTTCA ACCACCATCT CCGCTCGACT TGCATGCGTT    1420
AGGCACGCCG CCAGCGTTCG TCCTGA                                        1446
```

Figure 10

| Strain | Substrate + concentration | Incubation time | Lactate formed | Ethanol formed | Acetate formed |
|---|---|---|---|---|---|
| | mM or (mM monomer equivalent) | h | mM | mM | mM |
| DIB004C | Cellulose (26 mM) | 96 | 9,6 | 1,6 | 4,8 |
| | Cellobiose (25 mM) | 96 | 18,8 | 0,3 | 8,6 |
| | Glucose 25 mM | 96 | 19,6 | 1,2 | 6,4 |
| | Xylan (31 mM) | 96 | 13,2 | 1,5 | 9,6 |
| | Xylose 30 mM | 96 | 18,6 | 3,2 | 2,5 |
| | Poplar (12 mM)[1] | 168 | 12,5 | 2,1 | 7,4 |
| DIB041C | Cellulose (26 mM) | 168 | 14,3 | 2,7 | 10,2 |
| | Cellobiose (25 mM) | 72 | 15,1 | 1,7 | 8,4 |
| | Glucose 25 mM | 72 | 17,6 | 1,3 | 8,5 |
| | Xylan (31 mM) | 72 | 17,4 | 1,4 | 9,5 |
| | Xylose 30 mM | 72 | 16,9 | 1,2 | 8,9 |
| DIB087C | Cellulose (26 mM) | 168 | 7,4 | 1,9 | 12,9 |
| | Cellobiose (25 mM) | 72 | 8,1 | 1,6 | 10,8 |
| | Glucose (25 mM) | 72 | 7,1 | 1,8 | 14,4 |
| | Xylan (31 mM) | 72 | 8,3 | 1,4 | 13,7 |
| | Xylose 30 mM | 72 | 7,6 | 1,3 | 13,9 |
| DIB101C | Cellulose (26 mM) | 96 | 6,6 | 1,1 | 6,9 |
| | Cellobiose (25 mM) | 168 | 14,8 | 2,6 | 11,1 |
| | Glucose 25 mM | 168 | 12,7 | 1,5 | 9,7 |
| | Xylan (31 mM) | 96 | 9,4 | 2,2 | 10,0 |
| | Xylose 30 mM | 96 | 10,5 | 5,1 | 4,8 |
| | Poplar (12 mM)[1] | 168 | 6,9 | 2,7 | 10,2 |
| DIB103C | Cellulose (26 mM) | 168 | 15,3 | 2,0 | 7,1 |
| | Cellobiose (25 mM) | 72 | 15,7 | 1,1 | 6,8 |
| | Glucose (25 mM) | 72 | 17,5 | 1,1 | 6,7 |
| | Xylan (31 mM) | 72 | 15,9 | 1,1 | 6,2 |
| | Xylose 30 mM | 72 | 16,1 | 1,0 | 6,5 |
| DIB104C | Cellulose (26 mM) | 72 | 16,3 | 2,1 | 7,8 |
| | Xylose 30 mM | 72 | 16,6 | 1,6 | 8,6 |
| | Xylose 30 mM | 72 | 16,8 | 1,7 | 8,1 |
| | Xylan (31 mM) | 72 | 15,1 | 1,4 | 9,0 |
| | Xylose 30 mM | 72 | 12,9 | 1,4 | 10,1 |
| DIB107C | Cellulose (26 mM) | 168 | 14,3 | 2,4 | 9,5 |
| | Cellobiose (25 mM) | 72 | 17,4 | 1,6 | 6,4 |
| | Glucose 25 mM | 72 | 14,1 | 1,8 | 9,3 |
| | Xylan (31 mM) | 72 | 13,8 | 1,3 | 9,9 |
| | Xylose 30 mM | 72 | 12,6 | 1,2 | 9,7 |
| DSM8903 | Cellulose (26 mM) | 168 | 6,6 | 1,4 | 5,7 |
| | Cellobiose (25 mM) | 96 | 13,2 | 1,9 | 7,6 |
| | Glucose 25 mM | 96 | 14,2 | 1,7 | 7,8 |
| | Xylan (31 mM) | 96 | 7,7 | 1,8 | 10,2 |
| | Xylose 30 mM | 96 | 14,7 | 2,9 | 4,1 |
| [1]) pretreated poplar wood, no free sugars | | | | | |

Figure 11

| Steam pretreated substrates | | Lactic Acid [mM] | Acetic Acid [mM] | EtOH [mM] |
|---|---|---|---|---|
| Miscanthus | DIB004C | 2,1 | 11,1 | 1,8 |
| | DIB101C | 1,6 | 11,6 | 1,4 |
| Wheat straw | DIB004C | 1,1 | 10,7 | 1,4 |
| | DIB101C | 1,1 | 8,6 | 1,2 |
| Sugarcane bagasse | DIB004C | 2,1 | 11,1 | 3,4 |
| | DIB101C | 2,4 | 8,9 | 2,1 |
| Corn stalks | DIB004C | 2,1 | 13,6 | 2,5 |
| | DIB101C | 1,3 | 13,7 | 1,7 |
| Corn cobs | DIB004C | 4,6 | 15,5 | 3,5 |
| | DIB101C | 5,3 | 15,7 | 2,1 |
| Whole corn Plants | DIB004C | 1,4 | 11,4 | 2,3 |
| | DIB101C | 1,1 | 10,0 | 1,3 |
| Sweet sorghum plants | DIB004C | 1,9 | 10,4 | 1,9 |
| | DIB101C | 1,2 | 9,8 | 1,4 |
| Poplar wood | DIB004C | 3,1 | 10,0 | 2,5 |
| | DIB101C | 2,0 | 10,7 | 1,7 |
| Spruce wood | DIB004C | 3,3 | 9,2 | 4,1 |
| | DIB101C | 3,0 | 11,0 | 2,0 |
| Cotton stalks | DIB004C | 1,0 | 4,6 | 0,6 |
| | DIB101C | 0,8 | 4,1 | 0,3 |
| Avicel (untreated) | DIB004C | 9,3 | 21,6 | 3,4 |
| | DIB101C | 8,2 | 22,5 | 3,3 |

EXTREME THERMOPHILIC BACTERIA OF THE GENUS *CALDICELLULOSIRUPTOR*

CROSS REFERENCE TO RELATED APPLICATIONS

This is a continuation of U.S. patent application Ser. No. 14/342,712, now abandoned, which is a national phase entry of PCT/EP2012/068627 filed Sep. 21, 2012, which itself claims priority to U.S. provisional patent application Ser. No. 61/669,981, filed Jul. 10, 2012, now expired, EP patent application Ser. No 12175679,5, filed Jul. 10, 2012, U.S. provisional patent application Ser. No. 61/537,892, filed on Sep. 22, 2011, now expired, and EP patent application ser. no 11007706.2, filed on Sep. 22, 2011; the content of each is herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with the file "712_CON_APP_2015-10-12_SEQID" created on 12 Oct. 2015, filed on 12 Oct 2015 and having a size of 15 Kilobytes. The sequence listing contained in this ASCII formatted document forms part of the specification and is herein incorporated by reference.

FIELD OF THE DISCLOSURE

The present disclosure pertains to novel isolated cellulolytic extreme thermophilic bacterial cells belonging to the genus *Caldicellulosiruptor*, mutants thereof, isolated strains, microbial cultures and microbial compositions. The novel bacteria are in particular suitable for the production of fermentation products such as ethanol and lactic acid from lignocellulosic biomass.

BACKGROUND

In general, fermentation products are produced by degradation of starch-containing material into fermentable sugars by liquefaction and saccharification followed by conversion of the sugars directly or indirectly into the desired fermentation product using a fermenting organism.

However, the industry of producing fermentation products such as ethanol and lactic acid is facing the challenge of redirecting the production process from fermentation of relatively easily convertible but expensive starchy materials, to the complex but inexpensive lignocellulosic biomass such as plant biomass.

Unlike starch, which contains homogenous and easily hydrolysed polymers, lignocellulosic biomass contains variable amounts of cellulose, hemicellulose, lignin and small amounts of protein, pectin, wax and other organic compounds. Lignocellulosic biomass should be understood in its broadest sense, so that it apart from wood, agricultural residues, energy crops also comprises different types of waste from both industry and households. Cellulosic biomass is a vast poorly exploited resource, and in some cases a waste problem. However, hexoses from cellulose can be converted by yeast to fuel ethanol for which there is a growing demand. Pentoses from hemicellulose cannot yet be converted to ethanol commercially but several promising ethanologenic microorganisms with the capacity to convert pentoses and hexoses are under development.

Typically, the first step in utilization of lignocellulosic biomass is a pre-treatment step, in order to fractionate the components of lignocellulosic material and increase their surface area.

The pre-treatment method most often used is steam pretreatment, a process comprising heating of the lignocellulosic material by steam injection to a temperature of 130-230° C. Prior to or during steam pretreatment, a catalyst like mineral or organic acid or a caustic agent facilitating disintegration of the biomass structure can be added optionally.

Another type of lignocellulose hydrolysis is acid hydrolysis, where the lignocellulosic material is subjected to an acid such as sulphuric acid whereby the sugar polymers cellulose and hemicellulose are partly or completely hydrolysed to their constituent sugar monomers and the structure of the biomass is destroyed facilitating access of hydrolytic enzymes in subsequent processing steps.

A further method is wet oxidation wherein the material is treated with oxygen at 150-185° C. Either pretreatment can be followed by enzymatic hydrolysis to complete the release of sugar monomers. This pre-treatment step results in the hydrolysis of cellulose into glucose while hemicellulose is transformed into the pentoses xylose and arabinose and the hexoses glucose, mannose and galactose. Thus, in contrast to starch, the hydrolysis of lignocellulosic biomass results in the release of pentose sugars in addition to hexose sugars. This implies that useful fermenting organisms need to be able to convert both hexose and pentose sugars to desired fermentation products such as ethanol.

After the pre-treatment the lignocellulosic biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g. glucose, mannose, and galactose); and (4) the fermentation of pentose sugars (e.g., xylose and arabinose).

Each processing step can make the overall process more costly and, therefore, decrease the economic feasibility of producing biofuel or carbon-based chemicals from cellulosic biological material. Thus, there is a need to develop methods that reduce the number of processing steps needed to convert cellulosic biological material to biofuel and other commercially desirable materials.

The four biologically mediated transformations may occur in a single step in a process configuration called consolidated bioprocessing (CBP), which is distinguished from other less highly integrated configurations in that CBP does not involve a dedicated process step for cellulase and/or hemicellulase production. CBP offers the potential for higher efficiency than a processes requiring dedicated cellulase production in a distinct unit operation.

Therefore, the availability of novel microorganisms for converting lignocellulosic biomass material to carbon-based chemicals would be highly advantageous.

SUMMARY OF THE DISCLOSURE

The present invention relates to novel microorganisms, and compositions useful for processing lignocellulosic biomass.

In a first aspect, embodiments of the disclosure provide novel isolated cellulolytic thermophilic bacterial cells belonging to the genus *Caldicellulosiruptor*, in particular capable of producing high levels of lactic acid and/or ethanol from lignocellulosic biomass material.

Embodiments of this disclosure relate to an isolated *Caldicellulosiruptor* sp. cell comprising a 16S rDNA with a sequence selected form the group consisting of SEQ ID NO. 1, SEQ ID NO. 2, SEQ ID NO. 3, SEQ ID NO. 4, SEQ ID NO. 5, SEQ ID NO. 6 or SEQ ID NO 7, or homologues thereof.

In one aspect, embodiments of this disclosure relate to an isolated *Caldicellulosiruptor* sp. DIB004C, *Caldicellulosiruptor* sp. DIB041C, *Caldicellulosiruptor* sp. DIB087C, *Caldicellulosiruptor* sp. DIB101C, *Caldicellulosiruptor* sp. DIB103C, *Caldicellulosiruptor* sp. DIB104C or *Caldicellulosiruptor* sp. DIB107C, each respectively characterized by having a 16S rDNA sequence at least 99 to 100%, preferably 99.5 to 99.99 percent identical to SEQ ID NO. 1, SEQ ID NO. 2, SEQ ID NO. 3, SEQ ID NO. 4, SEQ ID NO. 5, SEQ ID NO. 6 or SEQ ID NO 7 as outlined in table 1.

In still another aspect the present invention relates to an isolated strain comprising a *Caldicellulosiruptor* sp. cell according to any of the preceding aspects.

In a further aspect, embodiments of this disclosure relate to microorganism of the strain *Caldicellulosiruptor* sp. DIB004C deposited as DSM 25177, a microorganism derived therefrom or a *Caldicellulosiruptor* sp. DIB004C homolog or mutant.

In a further aspect, embodiments of this disclosure relate to microorganism of the strain *Caldicellulosiruptor* sp. DIB041C deposited as DSM 25771, a microorganism derived therefrom or a *Caldicellulosiruptor* sp. DIB041C homolog or mutant.

In a further aspect, embodiments of this disclosure relate to microorganism of the strain *Caldicellulosiruptor* sp. DIB087C deposited as DSM 25772, a microorganism derived there from or a *Caldicellulosiruptor* sp. DIB087C homolog or mutant.

In a further aspect, embodiments of this disclosure relate to microorganism of the strain *Caldicellulosiruptor* sp. DIB101C deposited as DSM 25178, a microorganism derived there from or a *Caldicellulosiruptor* sp. DIB101C homolog or mutant.

In a further aspect, embodiments of this disclosure relate to microorganism of the strain *Caldicellulosiruptor* sp. DIB103C deposited as DSM 25773, a microorganism derived there from or a *Caldicellulosiruptor* sp. DIB103C homolog or mutant.

In a further aspect, embodiments of this disclosure relate to microorganism of the strain *Caldicellulosiruptor* sp. DIB104C deposited as DSM 25774, a microorganism derived there from or a *Caldicellulosiruptor* sp. DIB104C homolog or mutant.

In a further aspect, embodiments of this disclosure relate to microorganism of the strain *Caldicellulosiruptor* sp. DIB107C deposited as DSM 25775, a microorganism derived there from or a *Caldicellulosiruptor* sp. DIB107C homolog or mutant.

In another aspect the present disclosure relates to a method of producing a fermentation product comprising culturing a cell according to the disclosure or a strain according to the disclosure under suitable conditions.

In still another aspect, embodiments of this disclosure relate to methods for converting lignocellulosic biomass material to a biofuel or other carbon-based chemical, comprising the step of contacting the lignocellulosic biomass material with a microbial culture for a period of time at an initial temperature and an initial pH, thereby producing an amount of a biofuel and/or other carbon-based products; wherein the microbial culture comprises an extremely thermophilic microorganism of the genus *Caldicellulosiruptor*, in particular all microorganisms of the strain *Caldicellulosiruptor* sp. as listed in table 1 with their respective deposition numbers, microorganisms derived from either of these strains or mutants or homologues thereof.

In still another aspect, embodiments of this disclosure relate to methods of making ethanol from biomass material, wherein the method comprises combining a microbial culture and the biomass in a medium; and fermenting the biomass under conditions and for a time sufficient to produce ethanol, in a single step process as part of a consolidated bioprocessing (CBP) system, with a cell, strain, microbial culture and/or a microorganism according to the present disclosure under suitable conditions.

In still another aspect, embodiments of this disclosure relate to methods of making lactic acid from biomass material, wherein the method comprises combining a microbial culture and the biomass in a medium; and fermenting the biomass under conditions and for a time sufficient to produce lactic acid, a salt or an ester thereof, in a single step process as part of a consolidated bioprocessing (CBP) system, with a cell, strain, microbial culture and/or a microorganism according to the present disclosure under suitable conditions.

In still another aspect, embodiments of this disclosure relate to methods of making both ethanol and lactic acid from biomass material, wherein the method comprises combining a microbial culture and the biomass in a medium; and fermenting the biomass under conditions and for a time sufficient to produce ethanol and lactic acid, a salt or an ester of the latter, in a single step process as part of a consolidated bioprocessing (CBP) system, with a cell, strain, microbial culture and/or a microorganism according to the present disclosure under suitable conditions.

In still another aspect, embodiments of this disclosure relate to methods of making ethanol and/or lacticllactic acid from biomass material, wherein the method comprises combining a microbial culture and the biomass in a medium; and fermenting the biomass under conditions and for a time sufficient to produce ethanol and/or lactic acid, a salt or an ester of the latter, in a single step process as part of a consolidated bioprocessing (CBP) system, with a cell, strain, microbial culture and/or a microorganism according to the present disclosure under suitable conditions in combination with application of method suitable to in-situ remove both or either fermentation product from the fermentation broth. Suitable methods include but are not limited to distillation, mediated distillation, extraction and precipitation.

Further, embodiments of this disclosure relate to compositions for converting lignocellulosic biomass or a microbial culture comprising a cell, strain or microorganism according to the present disclosure.

Further, embodiments of this disclosure relate to the use of a cell, strain, microorganism and/or a microbial culture according to the present disclosure for the production of lactic acid, a salt or an ester thereof or for the production of ethanol.

Before the disclosure is described in detail, it is to be understood that this disclosure is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

To provide a comprehensive disclosure without unduly lengthening the specification, the applicant hereby incorporates by reference each of the patents and patent applications cited herein.

BRIEF DESCRIPTION OF THE DRAWINGS

FIG. 2 shows a 16S rDNA from *Caldicellulosiruptor* sp. DIB004C cell.

FIG. 3 shows a 16S rDNA from *Caldicellulosiruptor* sp. DIB041C cell.

FIG. 4 shows a 16S rDNA from *Caldicellulosiruptor* sp. DIB087C cell.

FIG. 5 shows a 16S rDNA from *Caldicellulosiruptor* sp. DIB101C cell.

FIG. 6 shows a 16S rDNA from *Caldicellulosiruptor* sp. DIB103C cell.

FIG. 7 shows a 16S rDNA from *Caldicellulosiruptor* sp. DIB104C cell.

FIG. 8 shows a 16S rDNA from *Caldicellulosiruptor* sp. DIB107C cell.

FIG. 10 shows a table indicating performance data from all strains listed in table 1 and reference strain *C. saccharolyticus* DSM8903 during cultivation on cellulose, cellobiose, glucose, xylan, xylose and pretreated lignocellulosic biomass.

FIG. 11 shows a table indicating performance data from strains DIB004C and DIB101C on various types of pretreated lignocellulosic biomass.

DETAILED DESCRIPTION OF THIS DISCLOSURE

Figure 1:
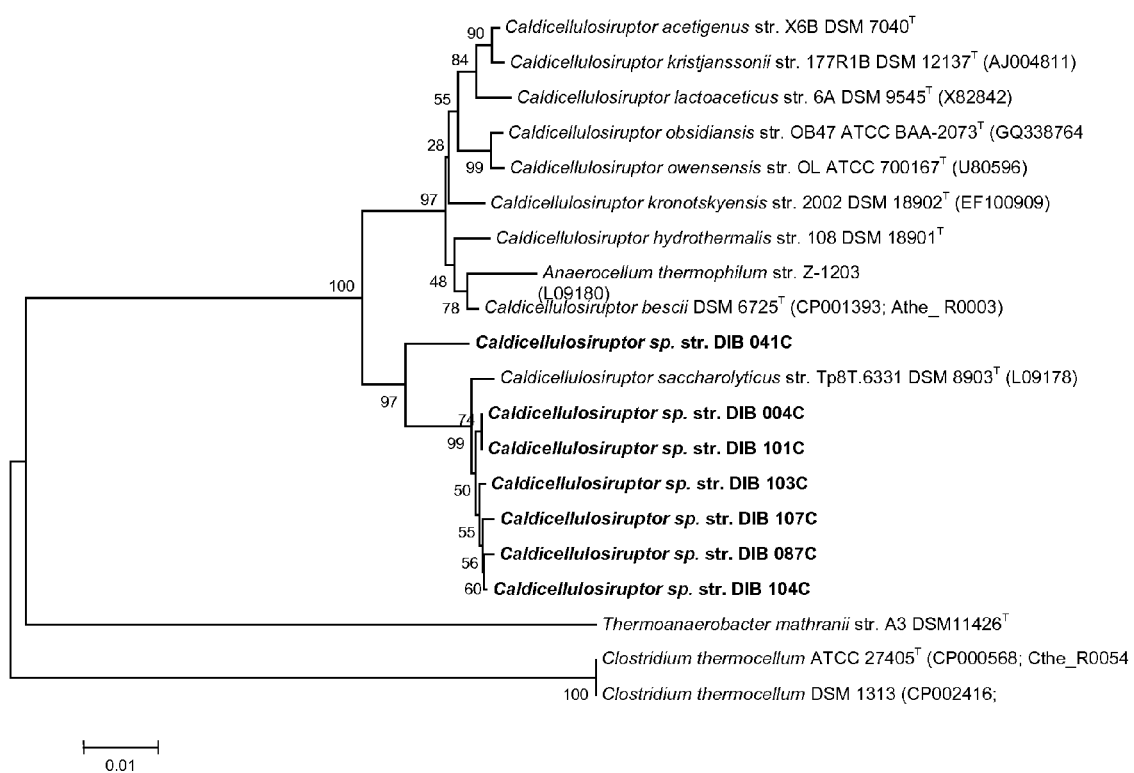
FIG. 1 illustrates a phylogenetic tree based on 16S rDNA genes for all *Caldicellulosiruptor* sp. strains comprised in the invention as listed in table 1

The present disclosure relates to methods, microorganisms, and compositions useful for processing lignocellulosic biomass. The disclosure relates, in certain aspects, to microorganisms which are able to convert lignocellulosic biomass such as, for example, *miscanthus* grass, to soluble products that can be used by the same or by another microorganism to produce an economically desirable product such as, for example, a biofuel (e.g., an alcohol and/or hydrogen gas (H2)), polymer, or commodity carbon-based chemical like lactic acid.

The application of this technology has the potential to render production of carbon-based chemicals and biofuels more economically feasible and to allow a broader range of microorganisms to utilize recalcitrant biomass. The use of cellulosic materials as sources of bioenergy is currently limited by typically requiring preprocessing of the cellulosic material. Such preprocessing methods can be expensive. Thus, methods that reduce dependence on preprocessing of cellulosic materials may have a dramatic impact on the economics of the use of recalcitrant biomass for biofuels production. One challenge in converting biomass into fermentation products is the recalcitrance and heterogeneity of the biological material.

The present inventors have found microorganisms of the genus *Caldicellulosiruptor* which have a variety of advantageous properties for their use in the conversion of ligno-cellulosic biomass material to biofuel and/or carbon-based chemicals, preferably to lactic acid, preferably in a single step process as part of a consolidated bioprocessing (CBP) system.

In particular, these microorganisms are extremely thermophilic and show a broad substrate specificities and high natural production of ethanol and lactic acid. Moreover, ethanol and lactic acid fermentation at high temperatures, for example over 70° C. has many advantages over mesophilic fermentation. One advantage of thermophilic fermentation is the minimization of the problem of contamination in batch cultures, fed-batch cultures or continuous cultures, since only a few microorganisms are able to grow at such high temperatures in un-detoxified lignocellulose biomass material.

It is also an advantage that the cells, strains and microorganisms according to the present disclosure grow on pre-treated as well as on untreated lignocellulosic biomass material.

The isolated cells, strains, microorganisms, compositions and microbial cultures are capable of growing and producing fermentation products on very high dry-matter concentrations of lignocellulosic biomass material.

In the present context the term "lignocellulosic biomass material" is intended to designate a untreated lignocellulosic biomass and/or a lignocellulosic biomass which has been subjected to a pretreatment step whereby lignocellulosic material has been at least partially separated into cellulose, hemicellulose and lignin thereby having increased the surface area and/or accessibility of the material. The lignocellulosic material may typically be derived from plant material, such as straw, hay, perennial grass, garden refuse, comminuted wood, fruit hulls and seed hulls.

The pretreatment method most often used is steam pretreatment, a process comprising heating of the lignocellulosic material by steam injection to a temperature of 130-230 degrees centigrade with or without subsequent sudden release of pressure. Prior to or during steam pretreatment, a catalyst like a mineral or organic acid or a caustic agent facilitating disintegration of the biomass structure can be added optionally. Catalysts often used for such a pretreatment include but are not limited to sulphuric acid, sulphurous acid, hydrochloric acid, acetic acid, lactic acid, sodium hydroxide (caustic soda), potassium hydroxide, calcium hydroxide (lime), ammonia or the respective salts or anhydrides of any of these agents.

Such steam pretreatment step may or may not be preceded by another treatment step including cooking of the biomass in water or steaming of the biomass at temperatures of 100-200° C. with or without the addition of a suitable catalyst like a mineral or organic acid or a caustic agent facilitating disintegration of the biomass structure. In between the cooking step and the subsequent steam pretreatment step one or more liquid-solid-separation and washing steps can be introduced to remove solubilized biomass components in order to reduce or prevent formation of inhibitors during the subsequent steam pretreatment step. Inhibitors formed during heat or steam pretreatment include but are not limited to furfural formed from monomeric pentose sugars, hydroxymethylfurfural formed from monomeric hexose sugars, acetic acid, levulinic acid, phenols and phenol derivatives.

Another type of lignocellulose hydrolysis is acid hydrolysis, where the lignocellulosic material is subjected to an acid such as sulfuric acid or sulfurous acid whereby the sugar polymers cellulose and hemicellulose are partly or completely hydrolysed to their constituent sugar monomers.

A third method is wet oxidation wherein the material is treated with oxygen at 150-185 degrees centigrade. The pretreatments can be followed by enzymatic hydrolysis to complete the release of sugar monomers. This pre-treatment step results in the hydrolysis of cellulose into glucose while hemicellulose is transformed into the pentoses xylose and arabinose and the hexoses glucose, mannose and galactose. The pretreatment step may in certain embodiments be supplemented with treatment resulting in further hydrolysis of the cellulose and hemicellulose. The purpose of such an additional hydrolysis treatment is to hydrolyze oligosaccharide and possibly polysaccharide species produced during the acid hydrolysis, wet oxidation, or steam pretreatment of cellulose and/or hemicellulose origin to form fermentable sugars (e.g. glucose, xylose and possibly other monosaccharides). Such further treatments may be either chemical or enzymatic. Chemical hydrolysis is typically achieved by treatment with an acid, such as treatment with aqueous sulphuric acid or hydrochloric acid, at a temperature in the range of about 100-150 degrees centigrade. Enzymatic hydrolysis is typically performed by treatment with one or more appropriate carbohydrase enzymes such as cellulases, glucosidases and hemicellulases including xylanases.

It has been found that the microorganisms according to the present disclosure can grow efficiently on various types of pretreated and untreated biomass (e.g. wood incl. poplar, spruce and cotton wood; various types of grasses and grass residues incl. *miscanthus*, wheat straw, sugarcane bagasse, corn stalks, corn cobs, whole corn plants, sweet sorghum).

As used herein "efficient" growth refers to growth in which cells may be cultivated to a specified density within a specified time.

The microorganisms according to the present disclosure can grow efficiently on crystalline cellulose and steam pretreated perennial grasses and grow efficiently on xylan. The main products when grown on untreated biomass substrates were lactate, for example, when the microorganisms grown on cellobiose and or xylane the lactate yield is high.

Cellobiose is a disaccharide derived from the condensation of two glucose molecules linked in a β(1→4) bond. It can be hydrolyzed to give glucose. Cellobiose has eight free alcohol (OH) groups, one ether linkage and two hemiacetal linkages, which give rise to strong inter- and intra-molecular hydrogen bonds. It is a type of dietary carbohydrate also found in mushrooms.

Xylan is a generic term used to describe a wide variety of highly complex polysaccharides that are found in plant cell walls and some algae. Xylans are polysaccharides made from units of xylose.

The microorganisms according to the present disclosure also can grow efficiently on spent biomass—insoluble material that remains after a culture has grown to late stationary phase (e.g., greater than $10^8$ cells/mL) on untreated biomass.

The microorganisms according to the present disclosure also grew efficiently on cellobiose, untreated switchgrass, and untreated poplar and poplar that had been heated at 98° C. for two minutes.

Furthermore, the microorganisms according to the present disclosure grew efficiently on both the soluble and insoluble materials obtained after heat-treating the biomass.

It was surprisingly found that the bacterial subspecies according to the present disclosure is capable of growing in a medium comprising a lignocellulosic biomass material having a dry-matter content of at least 10 percent wt/wt, such as at least 15 percent wt/wt, including at least 20 percent wt/wt, and even as high as at least 25 percent wt/wt.

The microorganisms according to the invention are anaerobic thermophile bacteria, and they are capable of growing at high temperatures even at or above 70 degrees centigrade The fact that the strains are capable of operating at this high temperature is of high importance in the conversion of the lignocellulosic material into fermentation products. The conversion rate of carbohydrates into e.g. lactic acid and/or ethanol is much faster when conducted at high temperatures. For example, the volumetric ethanol productivity of a thermophilic *Bacillus* is up to ten-fold higher than a conventional yeast fermentation process which operates at 30 degrees centigrade Consequently, a smaller production plant is required for a given plant capacity, thereby reducing plant construction costs. As also mentioned previously, the high temperature reduces the risk of contamination from other microorganisms, resulting in less downtime, increased plant productivity and a lower energy requirement for feedstock sterilization. The high operation temperature may also facilitate the subsequent recovery of the resulting fermentation products.

Lignocellulosic biomass material and lignocellulose hydrolysates contain inhibitors such as furfural, phenols and carboxylic acids, which can potentially inhibit the fermenting organism. Therefore, it is an advantage of the microorganisms according to the present disclosure that they are tolerant to these inhibitors.

The microorganisms according to the present disclosure are novel species of the genus *Caldicellulosiruptor* or novel subspecies of *Caldicellulosiruptor saccharolyticus*.

For example, the genus *Caldicellulosiruptor* includes different species of extremely thermophilic (growth at temperature significantly above 70° C.) cellulolytic and hemicellulolytic strictly anaerobic nonsporeforming bacteria. The first bacterium of this genus, *Caldicellulosiruptor saccharolyticus* strain Tp8T (DSM 8903) has a temperature optimum of 70° C. and was isolated from a thermal spring in New Zealand (Rainey et al. 1994; Sissons et al. 1987). It hydrolyses a variety of polymeric carbohydrates with the production of acetate, lactate and trace amounts of ethanol (Donnison et al. 1988). Phylogenetic analysis showed that it constitutes a novel lineage within the *Bacillus/Clostridium* subphylum of the Gram-positive bacteria (Rainey et al. 1994).

According to the present disclosure, the microorganisms produce ethanol and/or lactic acid and show several features that distinguish them from currently used microorganisms: (i) high yield and low product inhibition, (ii) simultaneous utilization of lignocellolytic biomass material and/or sugars, and (iii) growth at elevated temperatures. The microorganisms according to the present disclosure are robust thermophile organisms with a decreased risk of contamination. They efficiently convert an extraordinarily wide range of biomass components to carbon-based chemicals like lactic acid or ethanol.

As mentioned above, in one aspect, the present disclosure relates to an isolated cell comprising a 16S rDNA sequence selected from the group consisting of: SEQ ID NO 1, SEQ ID NO 2, SEQ ID NO 3, SEQ ID NO 4, SEQ ID NO 5, SEQ ID NO 6 and SEQ ID NO 7, and a combination of any thereof.

In one aspect, the present disclosure pertains to an isolated *Caldicellulosiruptor* sp. cell having a 16S rDNA sequence at least 99, at least 99.3, at least 99.5, at least, 99.7, at least 99.9, at least 99.99 percent identical to either sequence listed in table 1 or a combination thereof.

Each independently an embodiment of the invention is an isolated cell which is *Caldicellulosiruptor* sp. DIB004C (DSMZ Accession number 25177), an isolated cell which is *Caldicellulosiruptor* sp. DIB041C (DSMZ Accession number 25771), an isolated cell which is *Caldicellulosiruptor* sp. DIB087C (DSMZ Accession number 25772), an isolated cell which is *Caldicellulosiruptor* sp. DIB101C (DSMZ Accession number 25178), an isolated cell which is *Caldicellulosiruptor* sp. DIB103C (DSMZ Accession number 25773), an isolated cell which is *Caldicellulosiruptor* sp. DIB104C (DSMZ Accession number 25774) or an isolated cell which is *Caldicellulosiruptor* sp. DIB107C (DSMZ Accession number 25775), cells derived from either, mutants or a homolog of either.

As used herein "mutant" or "homolog" means a microorganism derived from the cells or strains according to the present disclosure, which are altered due to a mutation. A mutation is a change produced in cellular DNA, which can be spontaneous, caused by an environmental factor or errors in DNA replication, or induced by physical or chemical conditions. The processes of mutation included in this and indented subclasses are processes directed to production of essentially random changes to the DNA of the microorganism including incorporation of exogenous DNA. All mutants of the microorganisms comprise the advantages of being extreme thermophile (growing and fermenting at temperatures above 70° C.) and are capable of fermenting lignocellulosic biomass to ethanol and/or lactic acid. In an advantageous embodiment, mutants of the microorganisms according to the present disclosure have in a DNA-DNA hybridization assay, a DNA-DNA relatedness of at least 80%, preferably at least 90%, at least 95%, more preferred at least 98%, most preferred at least 99%, and most preferred at least 99.9% with one of the isolated bacterial strains *Caldicellulosiruptor* sp. DIB004C, DIB041C, DIB087C, DIB101C, DIB103C, DIB104C and DIB107C.

The invention is based on the isolated bacterial strains *Caldicellulosiruptor* sp. DIB004C, DIB041C, DIB087C, DIB101C, DIB103C, DIB104C and DIB107C that contain 16S rDNA sequences at least 99 to 100%, preferably 99.5 to 99.99, more preferably at least 99.99 percent identical to the respective sequences listed in table 1.

a) it is a microorganism of the genus *Caldicellulosiruptor*;
b) in a DNA-DNA hybridization assay, it shows a DNA-DNA relatedness of at least 70%, preferably at least 90%, at least 95%, more preferred at least 98%, most preferred at least 99% with either *Caldicellulosiruptor* sp. strain listed in table 1 with their respective accession numbers; and/or
c) it displays a level of 16S rDNA gene sequence similarity of at least 98%, preferably at least 99% or at least 99.5%, more preferably 100% with either either *Caldicellulosiruptor* sp. strain listed in table 1 with their respective accession numbers; and/or
d) it is capable of surviving in high temperature conditions above 75° C.
e) it is capable of surviving in high temperature conditions above 70° C., and or
f) it is a Gram-positive bacterium.

Preferably, at least two or at least three, and more preferred all of the above defined criteria a) to f) are fulfilled.

In an advantageous embodiment, the microorganisms according to the present disclosure in particular refer to a microorganism which belongs to the genus *Caldicellulosiruptor* and which preferably has one or more of the following characteristics:

a) It is a microorganism of the genus *Caldicellulosiruptor*
b) it is a microorganism of the species *Caldicellulosiruptor saccharolyticus*;
c) in a DNA-DNA hybridization assay, it shows a DNA-DNA relatedness of at least 80%, preferably at least 90%, at least 95%, more preferred at least 98%, most preferred at least 99%, and most preferred at least 99.9% with one of the strains of table 1; and/or
d) it displays a level of 16S rDNA gene sequence similarity of at least 98%, preferably at least 99%, at least 99.5% or at least 99.7%, more preferably 99.99% with one of the strains listed in table 1; and/or
e) it is capable of surviving and/or growing and/or producing a fermentation product selected from the group consisting of acids and alcohols at temperature conditions above 70° C., in particular of above 72° C.

TABLE 1

| Genus | Species | Name | DSMZ accession number | Deposition date | 16SrDNA SEQ ID NO. |
|---|---|---|---|---|---|
| *Caldicellulosiruptor* | sp. | DIB004C | DSM 25177 | Sep. 15, 2011 | 1 |
| *Caldicellulosiruptor* | sp. | DIB041C | DSM 25771 | Mar. 15, 2012 | 2 |
| *Caldicellulosiruptor* | sp. | DIB087C | DSM 25772 | Mar. 15, 2012 | 3 |
| *Caldicellulosiruptor* | sp. | DIB101C | DSM 25178 | Sep. 15, 2011 | 4 |
| *Caldicellulosiruptor* | sp. | DIB103C | DSM 25773 | Mar. 15, 2012 | 5 |
| *Caldicellulosiruptor* | sp. | DIB104C | DSM 25774 | Mar. 15, 2012 | 6 |
| *Caldicellulosiruptor* | sp. | DIB107C | DSM 25775 | Mar. 15, 2012 | 7 |

The strains listed in table 1 have been deposited in accordance with the terms of the Budapest Treaty on Sep. 15, 2011 with DSMZ—Deutsche Sammlung von Mikroorganismen and Zellkulturen GmbH, Inhoffenstr. 7B, 38124 Braunschweig, Germany, under the respectively indicated DSMZ accession numbers and deposition dates, respectively, by DIREVO Industrial Biotechnology GmbH, Nattermannallee 1, 50829 Cologne (DE).

The microorganisms of the species *Caldicellulosiruptor* sp. according to the present disclosure in particular refer to a microorganism which belongs to the genus *Caldicellulosiruptor* and which preferably has one or more of the following characteristics:

Preferably, at least two or at least three, and more preferred all of the above defined criteria a) to e) are fulfilled.

The term "DNA-DNA relatedness" in particularly refers to the percentage similarity of the genomic or entire DNA of two microorganisms as measured by the DNA-DNA hybridization/renaturation assay according to De Ley et al. (1970) Eur. J. Biochem. 12, 133-142 or Huβ et al. (1983) Syst. Appl. Microbiol. 4, 184-192. In particular, the DNA-DNA hybridization assay preferably is performed by the DSMZ (Deutsche Sammlung von Mikroorganismen und Zellkulturen GmbH, Braunschweig, Germany) Identification Service.

The term "16S rDNA gene sequence similarity" in particular refers to the percentage of identical nucleotides between a region of the nucleic acid sequence of the 16S ribosomal RNA (rDNA) gene of a first microorganism and the corresponding region of the nucleic acid sequence of the 16S rDNA gene of a second microorganism. Preferably, the region comprises at least 100 consecutive nucleotides, more preferably at least 200 consecutive nucleotides, at least 300 consecutive nucleotides or at least 400 consecutive nucleotides, most preferably about 480 consecutive nucleotides.

The strains according to disclosure have the potential to be capable of producing a number of different fermentation products, including acids, alcohols, ketones and hydrogen. In one embodiment, the alcohol is selected from ethanol, butanol, propanol, methanol, propanediol and butanediol. In a further embodiment the acid is lactic acid, propionic acid, acetic acid, succinic acid, butyric acid or formic acid and the ketone is acetone.

The *Caldicellulosiruptor* sp. strains according to the present disclosure have several highly advantageous characteristics needed for the conversion of lignocellulosic biomass material. Thus, these base strains possess all the genetic machinery for the hydrolysis of cellulose and hemicelluloses and for the conversion of both pentose and hexose sugars to various fermentation products such as lactic acid and ethanol. As will be apparent from the below examples, the examination of the complete 16S rDNA sequence showed that the closely related strains may all be related to *Caldicellulosiruptor saccharolyticus* although the 16S rDNA sequences may place them in a separate subspecies or even a different species Furthermore, the *Caldicellulosiruptor* sp. strains according to the present disclosure are cellulolytic and xylanolytic.

In a preferred embodiment, the *Caldicellulosiruptor* sp. microorganism is
a) *Caldicellulosiruptor* sp. DIB004C, deposited on Sep. 15, 2011 under the accession number DSM 25177 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE),
b) a microorganism derived from *Caldicellulosiruptor* sp. DIB004C or
c) a *Caldicellulosiruptor* sp. DIB004C mutant.

In another preferred embodiment, the *Caldicellulosiruptor* sp. microorganism is
a) *Caldicellulosiruptor* sp. DIB041C, deposited on Mar. 15, 2012 under the accession number DSM 25771 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE),
b) a microorganism derived from *Caldicellulosiruptor* sp. DIB041C or
c) a *Caldicellulosiruptor* sp. DIB041C mutant.

In another preferred embodiment, the *Caldicellulosiruptor* sp. microorganism is
a) *Caldicellulosiruptor* sp. DIB087C, deposited on Mar. 15, 2012 under the accession number DSM 25772 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE),
b) a microorganism derived from *Caldicellulosiruptor* sp. DIB087C or
c) a *Caldicellulosiruptor* sp. DIB087C mutant.

In another preferred embodiment, the *Caldicellulosiruptor* sp. microorganism is
a) *Caldicellulosiruptor* sp. DIB101C, deposited on Sep. 15, 2011 under the accession number DSM 25178 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE),
b) a microorganism derived from *Caldicellulosiruptor* sp. DIB101C or
c) a *Caldicellulosiruptor* sp. DIB101C mutant.

In another preferred embodiment, the *Caldicellulosiruptor* sp. microorganism is
a) *Caldicellulosiruptor* sp. DIB103C, deposited on Mar. 15, 2012 under the accession number DSM 25773 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE),
b) a microorganism derived from *Caldicellulosiruptor* sp. DIB103C or
c) a *Caldicellulosiruptor* sp. DIB103C mutant.

In another preferred embodiment, the *Caldicellulosiruptor* sp. microorganism is
a) *Caldicellulosiruptor* sp. DIB104C, deposited on Mar. 15, 2012 under the accession number DSM 25774 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE),
b) a microorganism derived from *Caldicellulosiruptor* sp. DIB104C or
c) a *Caldicellulosiruptor* sp. DIB104C mutant.

In another preferred embodiment, the *Caldicellulosiruptor* sp. microorganism is
a) *Caldicellulosiruptor* sp. DIB107C, deposited on Mar. 15, 2012 under the accession number DSM 25775 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE),
b) a microorganism derived from *Caldicellulosiruptor* sp. DIB107C or
c) a *Caldicellulosiruptor* sp. DIB107C mutant.

All strains listed above and in table 1 belong to the genus *Caldicellulosiruptor* and are strictly anaerobic, non-sporeforming, non-motile, gram-positive bacteria. Cells are straight rods 0.4-0.5 μm by 2.0-4.0 μm, occurring both singly and in pairs. After 7 days incubation at 72° C. on solid medium with agar and cellulose as substrate both strains form circular milky colonies of 0.5-1 mm in diameter. Clearing zones around the colonies are produced indicating cellulose degradation.

The term "a microorganism" as used herein may refer to only one unicellular organism as well as to numerous single unicellular organisms. For example, the term "a microorganism of the genus *Caldicellulosiruptor*" may refer to one single *Caldicellulosiruptor* bacterial cell of the genus *Caldicellulosiruptor* as well as to multiple bacterial cells of the genus *Caldicellulosiruptor*.

The terms "a strain of the genus *Caldicellulosiruptor*" and "a *Caldicellulosiruptor* cell" are used synonymously herein. In general, the term "a microorganism" refers to numerous cells. In particular, said term refers to at least $10^3$ cells, preferably at least $10^4$ cells, at least $10^5$ or at least $10^6$ cells.

As mentioned above lignocellolytic biomass according to the present disclosure can be but is not limited to grass, switch grass, cord grass, rye grass, reed canary grass, mixed prairie grass, miscanthus, Napier grass, sugar-methoding residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, pressmud from sugar beet, cotton stalk, banana leaves, oil palm residues and lignocellulosic biomass material obtained through processing of food plants. In advantageous embodiments, the lignocellulosic biomass material is hardwood and/or softwood, preferably poplar wood. In advantageous embodiments, the lignocellulosic biomass material is a grass or perennial grass, preferably miscanthus.

In advantageous embodiments, the lignocellulosic biomass material is subjected to mechanical, thermochemical, and/or biochemical pretreatment. The lignocellulosic biomass material could be exposed to steam treatment. In further embodiments, the lignocellulosic biomass material is pretreated with mechanical comminution and a subsequent treatment with lactic acid, acetic acid, sulfuric acid or sulfurous acid or their respective salts or anhydrides under heat and pressure with or without a sudden release of pressure. In another embodiment, the lignocellulosic biomass material is pretreated with mechanical comminution and a subsequent treatment with either sodium hydroxide, ammonium hydroxide, calcium hydroxide or potassium hydroxide under heat and pressure with or without a sudden release of pressure.

In advantageous embodiments, the lignocellulosic biomass material is pretreated with mechanical comminution and subsequent exposure to a multi-step combined pretreatment process. Such multi-step combined pretreatment may include a treatment step consisting of cooking in water or steaming of the lignocellulosic biomass material at a temperature of 100-200° C. for a period of time in between 5 and 120 min. Suitable catalysts including but not limited to lactic acid, acetic acid, sulfuric acid, sulfurous acid, sodium hydroxide, ammonium hydroxide, calcium hydroxide or potassium hydroxide or their respective salts or anhydrides may or may not be added to the process. The process may further include a step comprising a liquid-solid separation operation, e.g. filtration, separation, centrifugation or a combination thereof, separating the process fluid containing partially or fully hydrolyzed and solubilized constituents of the lignocellulosic biomass material from the remaining insoluble parts of the lignocellulosic biomass. The process may further include a step comprising washing of the remaining lignocellulosic biomass material. The solid material separated from solubilized biomass constituents may then be treated in a second step with steam under heat and pressure with or without a sudden release of pressure at a temperature of 150-250° C. for a period of time in between 1 and 15 min. In order to increase pretreatment effectiveness, a suitable catalyst including but not limited to lactic acid, acetic acid, sulfuric acid, sulfurous acid, sodium hydroxide, ammonium hydroxide, calcium hydroxide or potassium hydroxide or their respective salts or anhydrides may be added also to the second step.

In advantageous embodiments, the lignocellulosic biomass is milled before converted into biofuels like ethanol and/or carbon-based chemicals like lactic acid. In one embodiment, the lignocellulosic biomass is pretreated biomass from Populus sp, preferably pretreated with steam pretreatment or multi-step combined pretreatment. In another embodiment, the lignocellulosic biomass is pretreated biomass from any perennial grass, e.g. Miscanthus sp., preferably treated with steam pretreatment or multi-step combined pretreatment.

In advantageous embodiments the cells, strains, microorganisms may be modified in order to obtain mutants or derivatives with improved characteristics. Thus, in one embodiment there is provided a bacterial strain according to the disclosure, wherein one or more genes have been inserted, deleted or substantially inactivated. The variant or mutant is typically capable of growing in a medium comprising a lignocellulosic biomass material.

In another embodiment, there is provided a process for preparing variants or mutants of the microorganisms according to the present disclosure, wherein one or more genes are inserted, deleted or substantially inactivated as described herein.

In some embodiments one or more additional genes are inserting into the strains according to the present disclosure. Thus, in order to improve the yield of the specific fermentation product, it may be beneficial to insert one or more genes encoding a polysaccharase into the strain according to the invention. Hence, in specific embodiments there is provided a strain and a process according to the invention wherein one or more genes encoding a polysaccharase which is selected from cellulases (such as EC 3.2.1.4); beta-glucanases, including glucan-1,3 beta-glucosidases (exo-1,3 beta-glucanases, such as EC 3.2.1.58), 1,4-beta-cellobiohydrolases (such as EC 3.2.1.91) and endo-1,3(4)-beta-glucanases (such as EC 3.2.1.6); xylanases, including endo-1,4-beta-xylanases (such as EC 3.2.1.8) and xylan 1,4-beta-xylosidases (such as EC 3.2.1.37); pectinases (such as EC 3.2.1.15); alpha-glucuronidases, alpha-L-arabinofuranosidases (such as EC 3.2.1.55), acetylesterases (such as EC 3.1.1.-), acetylxylanesterases (such as EC 3.1.1.72), alpha-amylases (such as EC 3.2.1.1), beta-amylases (such as EC 3.2.1.2), glucoamylases (such as EC 3.2.1.3), pullulanases (such as EC 3.2.1.41), beta-glucanases (such as EC 3.2.1.73), hemicellulases, arabinosidases, mannanases including mannan endo-1,4-beta-mannosidases (such as EC 3.2.1.78) and mannan endo-1,6-alpha-mannosidases (such as EC 3.2.1.101), pectin hydrolases, polygalacturonases (such as EC 3.2.1.15), exopolygalacturonases (such as EC 3.2.1.67) and pectate lyases (such as EC 4.2.2.10), are inserted.

In accordance with the present disclosure, a method of producing a fermentation product comprising culturing a strain according to the invention under suitable conditions is also provided.

The strains according to the disclosure are strictly anaerobic microorganisms, and hence it is preferred that the fermentation product is produced by a fermentation process performed under strictly anaerobic conditions. Additionally, the strain according to invention is an extremely thermophillic microorganism, and therefore the process may perform optimally, when it is operated at temperature in the range of about 40-95 degrees centigrade, such as the range of about 50-90 degrees centigrade, including the range of about 60-85 degrees centigrade, such as the range of about 65-75 degrees centigrade For the production of certain fermentation products, it may be useful to select a specific fermentation process, such as batch fermentation process, including a fed-batch process or a continuous fermentation process. Also, it may be useful to select a fermentation reactor such as a stirred vessel reactor, an immobilized cell reactor, a fluidized bed reactor or a membrane bioreactor.

In accordance with the invention, the method is useful for the production of a wide range of fermentation products including acids, alcohols, ketones and hydrogen. Thus fermentation products such as ethanol, butanol, propanol, methanol, propanediol, butanediol, lactic acid, propionic acid, acetic acid, succinic acid, butyric acid, formic acid and acetone may be produced in accordance with the disclosure.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of".

The following methods and examples are offered for illustrative purposes only, and are not intended to limit the scope of the present disclosure in any way.

METHODS AND EXAMPLES

In the following examples, materials and methods of the present disclosure are provided including the determination of the properties of the microbial strains according to the present disclosure. It should be understood that these examples are for illustrative purpose only and are not to be construed as limiting this disclosure in any manner. All publications, patents, and patent applications cited herein are hereby incorporated by reference in their entirety for all purposes.

Example 1

Isolation and Cultivation

All procedures for enrichment and isolation of the strains listed in table 1 employed anaerobic technique for strictly anaerobic bacteria (Hungate 1969). The strains were enriched from environmental samples at temperatures higher than 70° C. with crystalline cellulose and beech wood as substrate. Isolation was performed by picking colonies grown on solid agar medium at 72° C. in Hungate roll tubes (Hungate 1969).

The cells are cultured under strictly anaerobic conditions applying the following medium:

| Basic medium | |
|---|---|
| NH4Cl | 1.0 g |
| NaCl | 0.5 g |
| MgSO4 × 7 H2O | 0.3 g |
| CaCl2 × 2 H2O | 0.05 g |
| NaHCO3 | 0.5 g |
| K2HPO4 | 1.5 g |
| KH2PO4 | 3.0 g |
| Yeast extract (bacto, BD) | 0.5 g |
| Cellobiose | 5.0 g |
| Vitamins (see below) | 1.0 ml |
| Trace elements (see below) | 0.5 ml |
| Resazurin | 1.0 mg |
| Na2S × 9 H2O | 0.75 g |
| Distilled water | 1000.0 ml |
| Trace elements stock solution | |
| $NiCl_2 \times 6H_2O$ | 2 g |
| $FeSO_4 \times 7H_2O$ | 1 g |
| NH4Fe(III) citrate, brown, 21.5% Fe | 10 g |
| $MnSO_4 \times H_2O$ | 5 g |
| $CoCl_2 \times 6H_2O$ | 1 g |
| $ZnSO_4 \times 7H_2O$ | 1 g |
| $CuSO_4 \times 5H_2O$ | 0.1 g |
| $H_3BO_3$ | 0.1 g |
| $Na_2MoO_4 \times 2H_2O$ | 0.1 g |
| $Na_2SeO_3 \times 5H_2O$ | 0.2 g |
| $Na_2WoO_4 \times 2H_2O$ | 0.1 g |
| Distilled water | 1000.0 ml |
| Add 0.5 ml of the trace elements stock solution to 1 liter of the medium | |
| Vitamine stock solution | |
| nicotinic acid | 200 mg |
| cyanocobalamin | 25 mg |
| p-aminobenzoic acid (4-aminobenzoic acid) | 25 mg |
| calcium D-pantothenate | 25 mg |
| thiamine-HCl | 25 mg |
| riboflavin | 25 mg |
| lipoic acid | 25 mg |
| folic acid | 10 mg |
| biotin | 10 mg |
| pyridoxin-HCl | 10 mg |
| Distilled water | 200.0 ml |
| Add 1 ml of the vitamine stock solution to 1 liter of the medium | |

All ingredients except sulfide are dissolved in deionized water and the medium is flushed with nitrogen gas (purity 99.999%) for 20 min at room temperature. After addition of sulfide, the pH-value is adjusted to 7.0 at room temperature with 1 M HCl. The medium is then dispensed into Hungate tubes or serum flasks under nitrogen atmosphere and the vessels are tightly sealed. After autoclaving at 121° C. for 20 min pH-value should be in between 6.8 and 7.0.

Carbon sources as specified for individual experiments are added prior to autoclaving. All applied substrate concentrations are indicated as glucose equivalents on the basis of available mol C (carbon).

Subsequent to autoclaving, cultures are inoculated by injection of a seed culture through the seal septum and inoculated in an incubator at 72° C. for the time indicated.

Example 2

HPLC

Sugars and fermentation products were quantified by HPLC-RI using a Via Hitachi LaChrom Elite (Hitachi corp.) fitted with an Rezex ROA Organic Acid H+ (Phenomenex). The analytes were separated isocratically with 2.5 mM $H_2SO_4$ and at 65° C.

Example 3

Phylogenetic Analysis of 16S rDNA Genes

Genomic DNA was isolated from cultures grown as described above and 16SrDNA amplified by PCR using 27F (AGAGTTTGATCMTGGCTCAG; SEQ ID No. 8) as forward and 1492R (GGTTACCTTGTTACGACTT; SEQ ID No. 9) as reverse primer. The resulting products were sequenced and the sequences analyzed using the Sequencher 4.10.1 software (Gene Codes Corporation). The NCBI database was used for BLAST procedures.

Sequencing of 16S rDNA from all strains listed in table 1 revealed all these had (at least) one copy of a 16S rDNA operon which was most closely related to *Caldicellulosiruptor saccharolyticus* (Strain Tp8T=DSM8903) in the available public databases. Alignment was carried out using ClustalW (Chenna et al. 2003) and the phylogenetic tree was constructed using software MEGA4 (Kumar et al. 2001). The tree for all strains listed in table 1 is displayed in FIG. 1.

The 16S rDNA sequences of all strains listed in table 1 have 99% percent identity to the respective sequence of e.g. *Caldicellulosiruptor saccharolyticus* (Strain Tp8T=DSM8903).

Example 4

Batch Experiments

Batch experiments with all strains were executed by cultivation on the medium described above with the carbon source substrates listed in FIGS. 10 and 11. Sealed Hungate tubes or serum flaks were used for cultivation in a standard incubator at a temperature of 72° C.

The results clearly show that all strains are capable to produce ethanol and lactic acid on soluble sugars, on soluble and insoluble sugar polymers as well as on the pretreated lignocellulose in the absence of free sugars.

Physiological comparison with the strain DSM8903 identified as the most closely related to the 16S rDNA comparison indicates a significantly higher ethanol and lactate formation in combination with a partially decreased production of acetate on polymeric substrates.

Example 5

Fermentation

Batch experiments with all strains, e.g. DIB004C, were performed by cultivation on the medium described above with addition of 20 g/L *miscanthus* grass pretreated with a suitable method selected from those described above comprising heating in the presence of dilute acid followed by sudden release of pressure.

Temperature is controlled to 72° C. and the pH-value is controlled to 6.75±0.1 throughout the fermentation. The fermenter is purged with nitrogen to remove excess oxygen before sodium sulphide is added as described above.

The fermentation is started by addition of a seed culture prepared as described in example 1.

The results of the HPLC analysis as described in example 2 show parallel production of ethanol, lactic acid and acetic acid.

Figure 9:
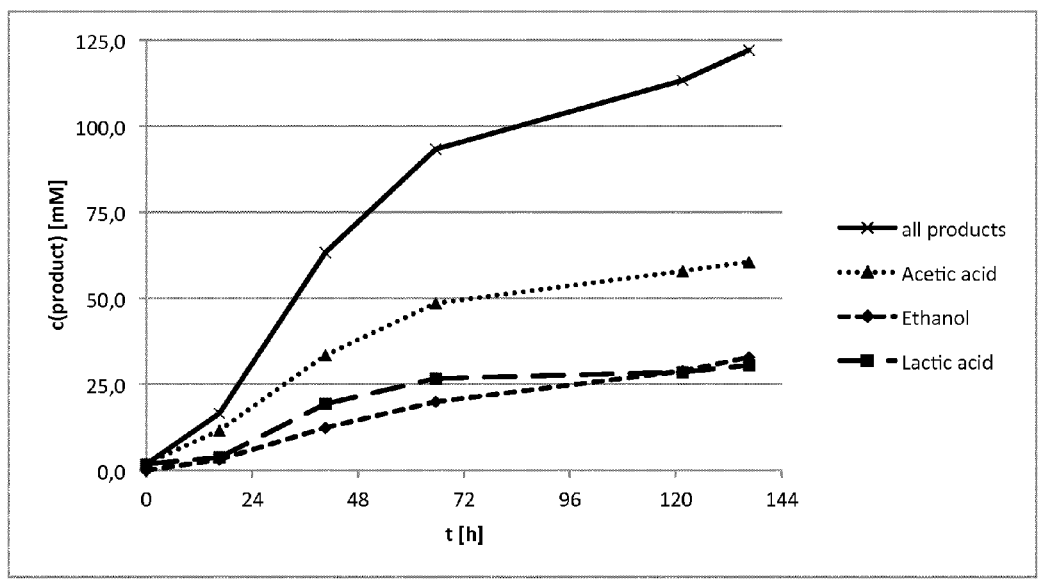
FIG. 9 shows a graph indicating production of ethanol and lactic acid by DIB004C during growth on steam-pretreated *miscanthus* grass.

The results of the product formation during a fermentation of *Caldicellulosiruptor* sp. DIB004C on pretreated *miscanthus* grass is shown in FIG. 9.

LIST OF ADDITIONAL REFERENCES

Rainey F A, Donnison A M, Janssen P H, Saul D, Rodrigo A, Bergquist P L, Daniel R M, Stackebrandt E, Morgan H W. (1994) Description of *Caldicellulosiruptor saccharolyticus* gen. nov., sp. nov: an obligately anaerobic, extremely thermophilic, cellulolytic bacterium. FEMS Microbiol Lett. 120:263-266.

Sissons C H, Sharrock K R, Daniel R M, Morgan H W. (1987) Isolation of cellulolytic anaerobic extreme thermophiles from New Zealand thermal sites. Appl Environ Microbiol. 53:832-838.

Donnison A M, Brockelsby C M, Morgan H W, Daniel R M. (1989) The degradation of lignocellulosics by extremely thermophilic microorganisms. Biotechnol Bioeng. 33:1495-1499.

Hungate R E. (1969) A roll tube method for cultivation of strict anaerobes. In: Methods in Microbiology Eds. Norris J R and Ribbons D W. pp 118-132. New York: Academic Press.

Chenna R, Sugawara H, Koike T, Lopez R, Gibson T J, Higgins D G, Thompson J D. (2003) Multiple sequence alignment with the Clustal series of programs. Nucleic Acids Res. 13:3497-3500.

Kumar S, Tamura K, Jakobsen I B, Nei M. (2001) MEGA2: molecular evolutionary genetics analysis software. Bioinformatics. 17:1244-1245.

---

What is claimed is:

1. A method for converting lignocellulosic biomass material to a carboxylic acid comprising:
    pretreating lignocellulosic biomass material, wherein the pretreatment is selected from the group consisting of:
    exposing the lignocellulosic biomass material to a steam treatment,
    mechanical comminution and a subsequent treatment of the lignocellulosic biomass material with sulfurous acid or its anhydride under heat and pressure with a sudden release of pressure,
    milling the lignocellulosic biomass material,
    exposing the lignocellulosic biomass material to cellulose and hemicellulose degrading enzymes, and
    contacting the lignocellulosic biomass material with a microbial culture for a period of time at an initial temperature and an initial pH, thereby producing an amount of a carboxylic acid, wherein the microbial culture comprises *Caldicellulosiruptor* sp. DIB004C, deposited as DSM 25177, and wherein the lignocellulosic biomass material is converted in a single step process as part of a consolidated bioprocessing (CBP) system.

2. The method according to claim 1, wherein the period of time is 10 hours to 300 hours.

3. The method according to claim 1, wherein the period of time is 50 hours to 200 hours.

4. The method according to claim 1, wherein the initial temperature is in the range between 55° C. and 80° C.

5. The method according to claim 1, wherein the initial pH is between 5 and 9.

6. The method according to claim 1, wherein the carboxylic acid is lactic acid or acetic acid.

7. The method according to claim 1, wherein the lignocellulosic biomass material is selected from the group consisting of grass, switch grass, cord grass, rye grass, reed canary grass, mixed prairie grass, miscanthus, sugar-methoding residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, and softwood, pressmud from sugar beet, cotton stalk, banana leaves, and lignocellulosic biomass material obtained through processing of food plants.

8. The method according to claim 1, wherein the lignocellulosic biomass material is selected from the group consisting of corn stover, sugarcane bagasse, cotton stalks, and switchgrass.

9. The method according to claim 1, wherein the lignocellulosic biomass material is a grass or perennial grass.

10. The method according to claim 1, wherein the step of pretreating the lignocellulosic biomass material comprises the exposing of the lignocellulosic biomass material to the steam treatment.

11. The method according to claim 1, wherein the step of pretreating the lignocellulosic biomass material comprises the mechanical comminution and the subsequent treatment with sulfurous acid or its anhydride under heat and pressure with the sudden release of pressure.

12. The method according to claim 1, wherein the step of pretreating the lignocellulosic biomass material comprises the milling of the lignocellulosic biomass.

13. The method according to claim 1, wherein the step of pretreating the lignocellulosic biomass material comprises the exposure to cellulose and hemicellulose degrading enzymes.

* * * * *

UNITED STATES PATENT AND TRADEMARK OFFICE
CERTIFICATE OF CORRECTION

PATENT NO. : 9,650,686 B2
APPLICATION NO. : 14/880743
DATED : May 16, 2017
INVENTOR(S) : Curvers and Svetlichnyi Page 1 of 1

It is certified that error appears in the above-identified patent and that said Letters Patent is hereby corrected as shown below:

In the Claims

At Column 29, Line 12, in Claim 1, please replace:
"milling the lignocellulosic biomass material,"
With the following:
-- milling the lignocellulosic biomass material, and --

Signed and Sealed this
Twelfth Day of June, 2018

Andrei Iancu
*Director of the United States Patent and Trademark Office*

SEQUENCE LISTING

```
<160> NUMBER OF SEQ ID NOS: 9

<210> SEQ ID NO 1
<211> LENGTH: 1396
<212> TYPE: DNA
<213> ORGANISM: Artificial Sequence
<220> FEATURE:
<223> OTHER INFORMATION: Caldicecellulosiruptor sp. 16SrDNA

<400> SEQUENCE: 1
ttacgacttc accccaatca tcagccccac cttcaacaca gcttaacctg tgtcttcagg     60
tgttgctgac tctcatggtg tgacgggcgg tgtgtacaag gcccgggaac gtattcaccg    120
cggcatgctg atccgcgatt actagcgatt ccgacttcat gcaggcgagt tgcagcctgc    180
aatccgaact gggggtgctt ttttgggatt cgctccggct cgcgccttcg cacgccctct    240
gtagcaccca ttgtagcacg tgtgtagccc agggcataag gggcatgatg atttgacgtc    300
atccccacct tcctccgcct catcgacggc agtcccctta gagtgcccac cattacgcgc    360
tggcaactaa gggcagggg tgcgctcgtt gcgggactta acccaacatc tcacgacacg    420
```

```
agctgacgac aaccatgcac cacctgtgtc cgggctcctg ctctcatcga acaggcaccc    480
caccctttcg ggcaggtccc cggcatgtca agccctggta aggttcttcg cgttgcttcg    540
aattaaacca catgctccac cgcttgtgcg ggccccgtc aattcctttg agtttcaacc     600
ttgcggccgt actccccagg cgggatgctt attgtgttaa ctacggcacg gaggagtcct    660
tctcccccac acctagcatc catcgtttac agcgtggact accagggtat ctaatcctgt    720
tcgctcccca cgctttcgtg cctcagcgtc agttacggtc cagacggccg ccttcgccac    780
tggtgttcct cccgatatct acgcatttca ccgctacacc gggaattccg ccgtcctctc    840
ccgcactcaa gctatgcagt attaagcgca atccttaggt tgagcctaag gctttcacgc    900
ttaactcgca tagccgccta cgcacccttt acgcccagta attccggaca acgctcgcca    960
cctacgtatt accgcggctg ctggcacgta gttagccgtg ctttttaaa cgggtactat    1020
ctcctacttc tccccgtcca aagaggttta caccccgaag ggcttcttcc ctcacgcggc   1080
gtcgctgcgt caggcttccg cccattgcgc aagattcccc gctgctgcct cccgtaggag   1140
tgtgggccgt gtctcagtcc cactgtggcc gtacaccctc tcaggccggc tacccgtcgt   1200
cgccttggta ggccgttacc ccaccaacta gctgatgggc cgcgagccca tcccagcca   1260
gtatagcctc cccggctacc ctttcaccac atcaccatgc gatgacgtgg tcccatcggg   1320
tattagcagc cctttcgagc tgttatcccc gtgctggggg taggttgctc acgtgttact   1380
cacccgtccg ccgcta                                                    1396
```

```
<210> SEQ ID NO 2
<211> LENGTH: 1480
<212> TYPE: DNA
<213> ORGANISM: Artificial Sequence
<220> FEATURE:
<223> OTHER INFORMATION: Caldicellulosiruptor sp. 16SrDNA

<400> SEQUENCE: 2
ctcaggacga acgctggcgg cgtgcctaac gcatgcaagt cgagcggagg tagccatgaa     60
ggtgaagagc tggagtggct atcttagcgg cggacgggtg agtaacacgt gagcaaccta    120
ccctcagcac ggggataaca gctcgaaagg ctgctaata cccgatggga ccacggcatc    180
gcatgatgtt gtggtgaaag ggtagccgtg gaggctatac cggctgggga tgggctcgcg    240
gcccatcagc tagttggtgg ggtaacggcc taccaaggct acgacgggta gccggcctga    300
gagggtggtc ggccacagtg ggactgagac acggcccaca ctcctacggg aggcagcagc    360
ggggaatctt gcgcaatggg cgaaagcctg acgcagcgac gccgcgtgag ggaggaagcc    420
cttcggggtg taaacctctt tggacgggga aaggaggag atagtacccg tttaaaaagc    480
cacggctaac tacgtgccag cagccgcggt aatacgtagg tggcgagcgt tgtccggaat    540
tactgggcgt aaagggtgcg taggcggcta tgcaagttaa gcgtgaaatc ttggggctca    600
accccaaggc tgcgcttaat actgcatagc ttgagtgcgg gagaggacgg cggaattccc    660
ggtgtagcgg tgaaatgcgt agatatcggg aggaacacca gtggcgaagg cggccgtctg    720
gaccgtaact gacgctgagg cacgaaagcg tgggagcga acaggattag ataccctggt    780
agtccacgct gtaaacgatg gatgctaggt gtggggagga aggactcctc cgtgccgtag    840
ttaacacaat aagcatcccg cctggggagt acggccgcaa ggttgaaact caaaggaatt    900
gacggggggcc cgcacaagcg gtggagcatg tggtttaatt cgaagcaacg cgaagaacct    960
taccagggct tgacatgccg ggaacctgcc cgaaagggtg gggtgcctgc gcgatgagtg   1020
```

```
caggagcccg acacaggtg gtgcatggtt gtcgtcagct cgtgtcgtga gatgttgggt     1080
taagtcccgc aacgagcgca acccctgccc ttagttgcca gcacgtaatg gtgggcactc     1140 taagggact gccgccgatg aggcggagga aggtggggat gacgtcaaat catcatgccc     1200
cttatgccct gggctacaca cgtgctacaa tgggtgctac agagggttgc gaaggcgcga     1260
gccggagcta atcccaaaaa agcacccca gttcggattg caggctgcaa ctcgcctgca     1320
tgaagtcgga atcgctagta atcgcggatc agcatgccgc ggtgaatacg ttcccgggcc     1380
ttgtacacac cgcccgtcac accatgagag tcagcaacac ctgaagacac agggcagctg     1440
tgttgaaggt ggggctgatg attggggtga agtcgtaaca                           1480

<210> SEQ ID NO 3
<211> LENGTH: 1481
<212> TYPE: DNA
<213> ORGANISM: Artificial Sequence
<220> FEATURE:
<223> OTHER INFORMATION: Caldicellulosiruptor sp. 16SrDNA

<400> SEQUENCE: 3
tcaggacgaa cgctggcggc gtgcctaacg catgcaagtc gagcggagat ggtggttgaa       60
ggtgatgagc tggaggctgc catcttagcg gcggacgggt gagtaacacg tgagcaacct      120 accccccagca cggggataac agctcgaaag gctgctaat acccgatggg accacgtcat      180
cgcatggtga tgtggtgaaa gggtagccgg ggaggctata ctggctgggg atgggctcgc      240
ggcccatcag ctagttggtg gggtaacggc tcaccaaggc gacgacgggt agccggcctg      300
agagggtgta cggccacagt gggactgaga cacggcccac actcctacgg gaggcagcag     360
cggggaatct tgcgcaatgg gcggaagcct gacgcagcga cgccgcgtga gggaagaagc     420
ccttcggggt gtaaacctct ttggacgggg agaagtagga gatagtaccc gtttaaaaag     480
ccacggctaa ctacgtgcca gcagccgcgg taatacgtag gtggcgagcg ttgtccggaa     540
ttactgggcg taaagggtgc gtaggcggct atgcgagtta agcgtgaaag ccttaggctc     600
aacctaagga ttgcgcttaa tactgcatag cttgagtgcg ggagaggacg gcggaattcc     660
cggtgtagcg gtgaaatgcg tagatatcgg aggaacacc agtggcgaag gcggccgtct     720
ggaccgtaac tgacgctgag gcacgaaagc gtggggagcg aacaggatta gataccctgg     780
tagtccacgc tgtaaacgat ggatgctagg tgtggggag aaggactctt ccgtgccgta     840
gttaacacaa taagcatccc gcctggggag tacggccgca aggttgaaac tcaaaggaat     900
tgacgggggc ccgcacaagc ggtggagcat gtggtttaat tcgaagcaac gcgaagaacc     960
ttaccagggc ttgacatgcc ggggacctgc ccgaaagggt ggggtgcctg ttcgatgaga    1020
gcaggaaccc ggacacaggt ggtgcatggt tgtcgtcagc tcgtgtcgtg agatgttggg    1080
ttaagtcccg caacgagcgc aaccctgcc cttagttgcc agcgggtaat ggtgggcact    1140
ctaaggggac tgccgtcgat gaggcggagg aaggtgggga tgacgtcaaa tcatcatgcc    1200
ccttatgccc tgggctacac acgtgctaca atgggtgcta cagagggcgt gcaaggcgc    1260 gagccggagc gaatcccaaa aaagcacccc cagttcggat tgcaggctgc aactcgcctg    1320
catgaagtcg gaatcgctag taatcgcgga tcagcatgcc gcggtgaata cgttcccggg    1380
ccttgtacac accgcccgtc acaccatgag agtcagcaac cctgaagac acaggttaag    1440 ctgtgttgaa ggtggggctg atgattgggg tgaagtcgta a                       1481

<210> SEQ ID NO 4
<211> LENGTH: 1212
```

<212> TYPE: DNA
<213> ORGANISM: Artificial Sequence
<220> FEATURE:
<223> OTHER INFORMATION: Caldicellulosiruptor sp. 16Sr DNA

<400> SEQUENCE: 4

```
cctgtgtctt caggtgttgc tgactctcat ggtgtgacgg gcggtgtgta caaggcccgg      60
gaacgtattc accgcggcat gctgatccgc gattactagc gattccgact tcatgcaggc     120
gagttgcagc ctgcaatccg aactgggggt gcttttttgg gattcgctcc ggctcgcgcc     180
ttcgcacgcc ctctgtagca cccattgtag cacgtgtgta gcccagggca taagggcat      240
gatgatttga cgtcatcccc accttcctcc gcctcatcga cggcagtccc cttagagtgc     300
ccaccattac gcgctggcaa ctaagggcag gggttgcgct cgttgcggga cttaacccaa     360
catctcacga cacgagctga cgacaaccat gcaccacctg tgtccgggct cctgctctca     420
tcgaacaggc accccaccct ttcgggcagg tccccggcat gtcaagccct ggtaaggttc     480
ttcgcgttgc ttcgaattaa accacatgct ccaccgcttg tgcgggcccc cgtcaattcc     540
tttgagtttc aaccttgcgg ccgtactccc caggcgggat gcttattgtg ttaactacgg     600
cacggaggag tccttctccc ccacacctag catccatcgt ttacagcgtg gactaccagg     660
gtatctaatc ctgttcgctc cccacgcttt cgtgcctcag cgtcagttac ggtccagacg     720
gccgccttcg ccactggtgt tcctcccgat atctacgcat ttcaccgcta caccgggaat     780
tccgccgtcc tctcccgcac tcaagctatg cagtattaag cgcaatcctt aggttgagcc     840
taaggctttc acgcttaact cgcatagccg cctacgcacc ctttacgccc agtaattccg     900
gacaacgctc gccacctacg tattaccgcg gctgctggca cgtagttagc cgtggctttt     960
taaacgggta ctatctccta cttctccccg tccaaagagg tttacacccc gaagggcttc    1020
ttccctcacg cggcgtcgct gcgtcaggct tccgcccatt gcgcaagatt ccccgctgct    1080
gcctcccgta ggagtgtggg ccgtgtctca gtcccactgt ggccgtacac cctctcaggc    1140
cggctacccg tcgtcgcctt ggtaggccgt taccccacca actagctgat gggccgcgag    1200
cccatcccca gc                                                        1212
```

<210> SEQ ID NO 5
<211> LENGTH: 1253
<212> TYPE: DNA
<213> ORGANISM: Artificial Sequence
<220> FEATURE:
<223> OTHER INFORMATION: Caldicellulosiruptor sp. 16SrDNA

<400> SEQUENCE: 5

```
cgacttcacc ccaatcatca gccccacctt caacacagct taacctgtgt cttcaggtgt      60
tgctgactct catggtgtga cgggcggtgt gtacaaggcc cgggaacgta ttcaccgcgg     120
catgctgatc cgcgattact agcgattccg acttcatgca ggcgagttgc agcctgcaat     180
ccgaactggg ggtgcttttt tgggattcgc tccggctcgc gccttcgcac gccctctgta     240
gcacccattg tagcacgtgt gtagcccagg gcataagggg catgatgatt tgacgtcatc     300
cccaccttcc tccgcctcat cgacggcagt cccttagag tgccaccat tacgcgctgg       360
caactaaggg caggggttgc gctcgttgcg ggacttaacc caacatctca cgacacgagc     420
tgacgacaac catgcaccac ctgtgtccgg gctcctgctc tcatcgaaca ggcaccccac     480
cctttcgggc aggtccccgg catgtcaagc cctggtaagg ttcttcgcgt tgcttcgaat     540
taaaccacat gctccaccgc ttgtgcgggc ccccgtcaat tcctttgagt ttcaaccttg     600
```

```
cggccgtact ccccaggcgg gatgcttatt gtgttaacta cggcacggag gagtccttct    660
cccccacacc tagcatccat cgtttacagc gtggactacc agggtatcta atcctgttcg    720
ctccccacgc tttcgtgcct cagcgtcagt tacggtccag acggccgcct tcgccactgg    780
tgttcctccc gatatctacg catttcaccg ctacaccggg aattccgccg tcctctcccg    840
cactcaagct atgcagtatt aagcgcaatc cttaggttga gcctaaggct ttcacgctta    900
actcgcatag ccgcctacgc acccttacg  cccagtaatt ccggacaacg ctcgccacct    960
acgtattacc gcggctgctg gcacgtagtt agccgtggct ttttaaacgg gtactatctc   1020
ctacttctcc ccgtccaaag aggtttacac cccgaagggc ttcttccctc acgcggcgtc   1080
gctgcgtcag gcttccgccc attgcgcaag attccccgct gctgcctccc gtaggagtgt   1140
gggccgtgtc tcagtcccac tgtggccgta caccctctca ggccggctac ccgtcgtcgc   1200
cttggtaagc cgttacccca caactagct  gatgggccgc gagcccatcc cca          1253
```

<210> SEQ ID NO 6
<211> LENGTH: 1255
<212> TYPE: DNA
<213> ORGANISM: Artificial Sequence
<220> FEATURE:
<223> OTHER INFORMATION: Caldicellulosiruptor sp. 16SrDNA

<400> SEQUENCE: 6

```
gacttcaccc caatcatcag ccccaccttc aacacagctt aacctgtgtc ttcaggtgtt     60
gctgactctc atggtgtgac gggcggtgtg tacaaggccc gggaacgtat tcaccgcggc    120
atgctgatcc gcgattacta gcgattccga cttcatgcag cgagttgca  gcctgcaatc    180 cgaactgggg gtgctttttt gggattcgct ccggctcgcg ccttcgcacg ccctctgtag    240
cacccattgt agcacgtgtg tagcccaggg cataaggggc atgatgattt gacgtcatcc    300
ccaccttcct ccgcctcatc gacggcagtc cccttagagt gcccaccatt acgcgctggc    360
aactaagggc aggggttgcg ctcgttgcgg gacttaaccc aacatctcac gacacgagct    420
gacgacaacc atgcaccacc tgtgtccggg ctcctgctct catcgaacag gcaccccacc    480
ctttcgggca ggtccccggc atgtcaagcc tggtaaggt  tcttcgcgtt gcttcgaatt    540
aaaccacatg ctccaccgct tgtgcgggcc cccgtcaatt cctttgagtt caaccttgc     600 ggccgtactc cccaggcggg atgcttattg tgttaactac ggcacggaag agtccttctc    660
ccccacacct agcatccatc gtttacagcg tggactacca gggtatctaa tcctgttcgc    720
tccccacgct ttcgtgcctc agcgtcagtt acggtccaga cggccgcctt cgccactggt    780
gttcctcccg atatctacgc atttcaccgc tacaccggga attccgccgt cctctcccgc    840
actcaagcta tgcagtatta agcgcaatcc ttaggttgag cctaaggctt tcacgcttaa    900
ctcgcatagc cgcctacgca ccctttacgc ccagtaattc cggacaacgc tcgccaccta    960
cgtattaccg cggctgctgg cacgtagtta gccgtggctt tttaaacggg tactatctcc   1020
tacttctccc cgtccaaaga ggtttacacc ccgaagggct tcttccctca cgcggcgtcg   1080
ctgcgtcagg cttccgccca ttgcgcaaga ttccccgctg ctgcctcccg taggagtgtg   1140
ggccgtgtct cagtcccact gtggccgtac accctctcag gccggctacc cgtcgtcgcc   1200
ttggtgagcc gttacccc ac caactagctg atgggccgcg agcccatccc cagcc        1255
```

<210> SEQ ID NO 7
<211> LENGTH: 1466
<212> TYPE: DNA
<213> ORGANISM: Artificial Sequence

```
<220> FEATURE:
<223> OTHER INFORMATION: Caldicellulosiruptor sp. 16SrDNA

<400> SEQUENCE: 7
gacttcaccc ccaatcatca gccccacctt caacacagct taacctgtgt cttcaggtgt      60
tgctgactct catggtgtga cgggcggtgt gtacaaggcc cgggaacgta ttcaccgcgg     120
catgctgatc cgcgattact agcgattccg acttcatgca ggcgagttgc agcctgcaat     180
ccgaactggg ggtgcttttt tgggattcgc tccggctcgc gccttcgcac gccctctgta     240
gcacccattg tagcacgtgt gtagcccagg gcataagggg catgatgatt tgacgtcatc     300
cccaccttcc tccgcctcat cgacggcagt cccctagag tgcccaccat tacgcgctgg      360
caactaaggg caggggttgc gctcgttgcg ggacttaacc caacatctca cgacacgagc     420
tgacgacaac catgcaccac ctgtgtccgg gctcctgctc tcatcgaaca ggcaccccac     480
cctttcgggc aggtccccgg catgtcaagc cctggtaagg ttcttcgcgt tgcttcgaat     540
taaaccacat gctccaccgc ttgtgcgggc cccgtcaat tcctttgagt ttcaaccttg      600
cggccgtact ccccaggcgg gatgcttatt gtgttaacta cggcacggag gagtccttct     660
cccccacacc tagcatccat cgtttacagc gtggactacc agggtatcta atcctgttcg     720
ctccccacgc tttcgtgcct cagcgtcagt tacggtccag acggccgcct tcgccactgg     780
tgttcctccc gatatctacg catttcaccg ctacaccggg aattccgccg tcctctcccg     840
cactcaagct atgcagtatt aagcgcaatc cttaggttga gcctaaggct ttcacgctta     900
actcgcatag ccgcctacgc accctttacg cccagtaatt ccggacaacg ctcgccacct     960
acgtattacc gcggctgctg gcacgtagtt agccgtggct ttttaaacgg gtactatctc    1020
ctacttctcc ccgtccaaag aggtttacac cccgaagggc ttcttccctc acgcggcgtc    1080
gctgcgtcag gcttccgccc attgcgcaag attccccgct gctgcctccc gtaggagtgt    1140
gggccgtgtc tcagtcccac tgtggccgta caccctctca ggccggctac ccgtcgtcgc    1200
cttggtgagc cgttacctca ccaactagct gatgggccgc gagcccatcc ccagccggat    1260
tactcctttc accacatcac catgcgatga cgtggtccca tcgggtatta gcagcccttt    1320
cgagctgtta tccccgtgct gggggtaggt tgctcacgtg ttactcaccc gtccgccgct    1380
aagatggcag cctccagctc atcaccttca accaccatct ccgctcgact tgcatgcgtt    1440
aggcacgccg ccagcgttcg tcctga                                         1466

<210> SEQ ID NO 8
<211> LENGTH: 20
<212> TYPE: DNA
<213> ORGANISM: Artificial Sequence
<220> FEATURE:
<223> OTHER INFORMATION: Primer for 16SrDNA amplification

<400> SEQUENCE: 8
agagtttgat cmtggctcag                                                  20

<210> SEQ ID NO 9
<211> LENGTH: 19
<212> TYPE: DNA
<213> ORGANISM: Artificial Sequence
<220> FEATURE:
<223> OTHER INFORMATION: 16SrDNA reverse primer

<400> SEQUENCE: 9
ggttaccttg ttacgactt                                                   19
```